United States Patent
Fiebig et al.

(10) Patent No.: US 9,717,483 B2
(45) Date of Patent: Aug. 1, 2017

(54) ACCESS CHAMBER AND MARKERS FOR BIOPSY DEVICE

(71) Applicant: DEVICOR MEDICAL PRODUCTS, INC., Cincinnati, OH (US)

(72) Inventors: Kevin M. Fiebig, Cincinnati, OH (US); Jessica P. Leimbach, Cincinnati, OH (US); Kyle P. Moore, Woodstock, GA (US); Morgan R. Hunter, Cincinnati, OH (US); Andrew P. Nock, Dayton, OH (US)

(73) Assignee: DEVICOR MEDICAL PRODUCTS, INC., Cincinnati, OH (US)

( * ) Notice: Subject to any disclaimer, the term of this patent is extended or adjusted under 35 U.S.C. 154(b) by 0 days.

(21) Appl. No.: 15/187,357

(22) Filed: Jun. 20, 2016

(65) Prior Publication Data
US 2016/0302779 A1    Oct. 20, 2016

Related U.S. Application Data

(63) Continuation of application No. 14/568,488, filed on Dec. 12, 2014, now Pat. No. 9,370,402, which is a
(Continued)

(51) Int. Cl.
*A61B 10/02* (2006.01)
*A61M 37/00* (2006.01)
(Continued)

(52) U.S. Cl.
CPC ...... *A61B 10/0275* (2013.01); *A61B 10/0096* (2013.01); *A61B 10/0283* (2013.01);
(Continued)

(58) Field of Classification Search
CPC ............ A61B 10/0275; A61B 10/0096; A61B 10/0283; A61B 10/02; A61B 37/0069;
(Continued)

(56) References Cited

U.S. PATENT DOCUMENTS

| 5,526,822 A | 6/1996 | Burbank et al. |
| 5,843,093 A | 12/1998 | Howard, III |

(Continued)

FOREIGN PATENT DOCUMENTS

| CN | 1676106 A | 10/2005 |
| CN | 1917910 A | 2/2007 |

(Continued)

OTHER PUBLICATIONS

Australian Office Action of related Australian Patent Application No. 2012294829 dated Jul. 21, 2015.
(Continued)

*Primary Examiner* — Bo J Peng
(74) *Attorney, Agent, or Firm* — Arent Fox LLP

(57) ABSTRACT

A marker deployment tool may comprise a marker cannula having a lateral deployment aperture, a push rod slidably disposed within the marker cannula and a scalloped tip coupled to the distal end of the marker cannula. The scalloped tip may have a push rod recess configured to receive a portion of the distal end of the push rod such that the push rod does not appreciably extend out of the lateral deployment aperture when the push rod is actuated distally. The marker deployment tool may further comprise a magnet at or near the distal end. This magnet may be used in combination with a magnet or plurality of magnets disposed about an access chamber in a tissue sample holder to assist the user in aligning the marker deployment tool. The access chamber in the tissue sample holder may also include a valve, two valves, or a removable plug.

10 Claims, 14 Drawing Sheets

Related U.S. Application Data continuation of application No. 13/205,189, filed on Aug. 8, 2011, now Pat. No. 8,938,285.

(51) Int. Cl.
- *A61B 17/34* (2006.01)
- *A61B 10/00* (2006.01)
- *A61B 90/00* (2016.01)

(52) U.S. Cl.
CPC .......... *A61B 17/34* (2013.01); *A61B 17/3468* (2013.01); *A61B 90/39* (2016.02); *A61M 37/0069* (2013.01); *A61B 10/02* (2013.01); *A61B 2010/0208* (2013.01); *A61B 2010/0225* (2013.01); *A61B 2017/3454* (2013.01); *A61B 2017/3456* (2013.01); *A61B 2090/392* (2016.02); *A61B 2090/3966* (2016.02); *A61B 2090/3983* (2016.02); *A61B 2090/3987* (2016.02)

(58) Field of Classification Search
CPC ..... A61B 17/34; A61B 17/3468; A61B 90/39; A61B 2010/0208; A61B 2010/0225; A61B 2017/3456; A61B 2017/3454; A61B 2090/3983; A61B 2090/392; A61B 2090/3966; A61B 2090/398

See application file for complete search history.

(56) References Cited

U.S. PATENT DOCUMENTS

| | | | |
|---|---|---|---|
| 5,993,399 | A | 11/1999 | Pruitt et al. |
| 6,086,544 | A | 7/2000 | Hibner et al. |
| 6,139,508 | A | 10/2000 | Simpson et al. |
| 6,228,055 | B1 | 5/2001 | Foerster et al. |
| 6,261,302 | B1 | 7/2001 | Voegele et al. |
| 6,371,904 | B1 | 4/2002 | Sirimanne et al. |
| 6,575,991 | B1 | 6/2003 | Chesbrough et al. |
| 6,993,375 | B2 | 1/2006 | Burbank et al. |
| 6,996,433 | B2 | 2/2006 | Burbank et al. |
| 7,044,957 | B2 | 5/2006 | Foerster et al. |
| 7,047,063 | B2 | 5/2006 | Burbank et al. |
| 7,229,417 | B2 | 6/2007 | Foerster et al. |
| 7,465,279 | B2 | 12/2008 | Beckman et al. |
| 7,938,786 | B2 | 5/2011 | Ritchie et al. |
| 2003/0109803 | A1 | 6/2003 | Huitema et al. |
| 2005/0065453 | A1 | 3/2005 | Shabaz et al. |
| 2005/0137498 | A1 | 6/2005 | Sakal et al. |
| 2006/0074345 | A1 | 4/2006 | Hibner |
| 2006/0116573 | A1 | 6/2006 | Field et al. |
| 2007/0118048 | A1 | 5/2007 | Stephens et al. |
| 2007/0142725 | A1 | 6/2007 | Hardin et al. |
| 2008/0195066 | A1 | 8/2008 | Speeg et al. |
| 2008/0214955 | A1 | 9/2008 | Speeg et al. |
| 2008/0228103 | A1 | 9/2008 | Ritchie et al. |
| 2008/0234715 | A1 | 9/2008 | Pesce et al. |
| 2009/0088665 | A1 | 4/2009 | Beckman et al. |
| 2009/0171242 | A1 | 7/2009 | Hibner |
| 2009/0209854 | A1 | 8/2009 | Parihar et al. |
| 2009/0270725 | A1 | 10/2009 | Leimbach et al. |
| 2010/0049084 | A1 | 2/2010 | Nock et al. |
| 2010/0049085 | A1 | 2/2010 | Nock et al. |
| 2010/0152610 | A1 | 6/2010 | Parihar et al. |
| 2010/0160817 | A1 | 6/2010 | Parihar et al. |
| 2010/0160819 | A1 | 6/2010 | Parihar |
| 2010/0317992 | A1 | 12/2010 | Leimbach et al. |
| 2010/0317993 | A1 | 12/2010 | Leimbach et al. |
| 2010/0317994 | A1 | 12/2010 | Leimbach |
| 2010/0317997 | A1 | 12/2010 | Hibner et al. |
| 2011/0071391 | A1 | 3/2011 | Speeg |
| 2011/0071423 | A1 | 3/2011 | Speeg et al. |
| 2011/0071424 | A1 | 3/2011 | Nock et al. |
| 2011/0071431 | A1 | 3/2011 | Speeg et al. |
| 2012/0109007 | A1 | 5/2012 | Rhad et al. |
| 2012/0265095 | A1 | 10/2012 | Fiebig |
| 2012/0283563 | A1 | 11/2012 | Moore et al. |
| 2012/0310110 | A1 | 12/2012 | Rhad et al. |

FOREIGN PATENT DOCUMENTS

| | | |
|---|---|---|
| CN | 101641052 A | 2/2010 |
| JP | 2003-210467 A | 7/2003 |
| JP | 2005-288175 A | 10/2005 |
| JP | 2008-523909 A | 7/2008 |
| WO | WO 2007/069105 A2 | 6/2007 |

OTHER PUBLICATIONS

Chinese Office Action of related Chinese Patent Application No. 201280038732.9 dated Mar. 25, 2016.
Chinese Office Action of related Chinese Patent Application No. 201280038732.9 dated May 27, 2015.
Chinese Search Report issued in Chinese Patent Application No. 201280038732.9 dated May 14, 2015.
Extended European Search Report issued in related European Patent Application No. 12822179.3 dated Apr. 15, 2015.
Chinese Office Action of related Chinese Patent Application No. 201280038732.9 dated Aug. 24, 2016.
Japanese Office Action of related Japanese Patent Application No. 2014-525037 dated Jun. 28, 2016.

ACCESS CHAMBER AND MARKERS FOR BIOPSY DEVICE

CROSS-REFERENCE TO RELATED APPLICATIONS

This application is a Continuation of U.S. patent application Ser. No. 14/568,488, filed Dec. 12, 2014 (now U.S. Pat. No. 9,370,402 issued Jun. 21, 2016), which is a Continuation of U.S. patent application Ser. No. 13/205,189, filed Aug. 8, 2011 (now U.S. Pat. No. 8,938,285 issued Jan. 20, 2015). The disclosures of the priority applications are incorporated in their entirety herein by reference.

BACKGROUND

Biopsy samples have been obtained in a variety of ways in various medical procedures using a variety of devices. Biopsy devices may be used under simple visual guidance, palpatory guidance, stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; U.S. patent application Ser. No. 12/953,715, entitled "Handheld Biopsy Device with Needle Firing," filed Nov. 24, 2010; U.S. patent application Ser. No. 13/086,567, entitled "Biopsy Device with Motorized Needle Firing," filed Apr. 14, 2011; U.S. patent application Ser. No. 13/099,497, entitled "Biopsy Device with Manifold Alignment Feature and Tissue Sensor," filed May 3, 2011; and U.S. patent application Ser. No. 13/150,950, entitled "Needle Assembly and Blade Assembly for Biopsy Device," filed Jun. 1, 2011. The disclosure of each of the above-cited U.S. Patents, U.S. Patent Application Publications, and U.S. Non-Provisional Patent Applications is incorporated by reference herein.

In some settings, it may be desirable to mark the location of a biopsy site for future reference. Moreover, it may be preferable to be able to access the biopsy site while the biopsy device is still located within the patient to accurately mark the biopsy site. Accordingly, one or more markers may be deposited at a biopsy site before, during, or after a tissue sample is taken from the biopsy site.

In some instances, biopsy devices have been adapted to allow for marking from a side-entry into the biopsy probe. Depending upon the location of the access point and the clearance through the device, the marker deployment device may be a flexible, semi-rigid, or a rigid deployment device. Some merely exemplary marker deployment tools include the MAMMOMARK™, MICROMARK®, and COR-MARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pub. No. 2011/0071431, entitled "Biopsy Marker Delivery Device," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. Patents and U.S. Patent Application Publications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
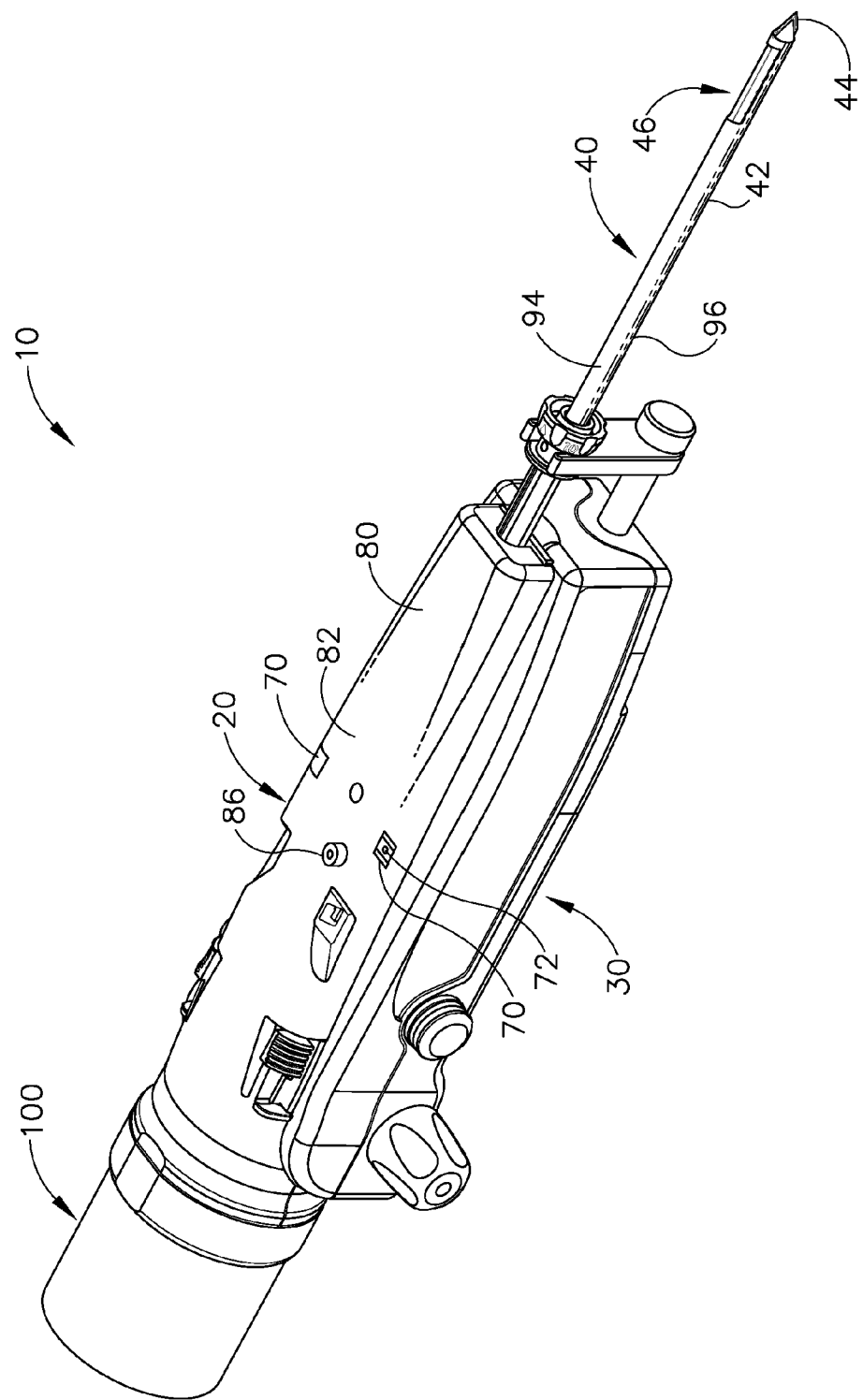
FIG. 1 depicts a perspective view of an exemplary biopsy device showing an exemplary probe coupled to an exemplary holster.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

1. Overview of Exemplary Biopsy Device

Figure 2:
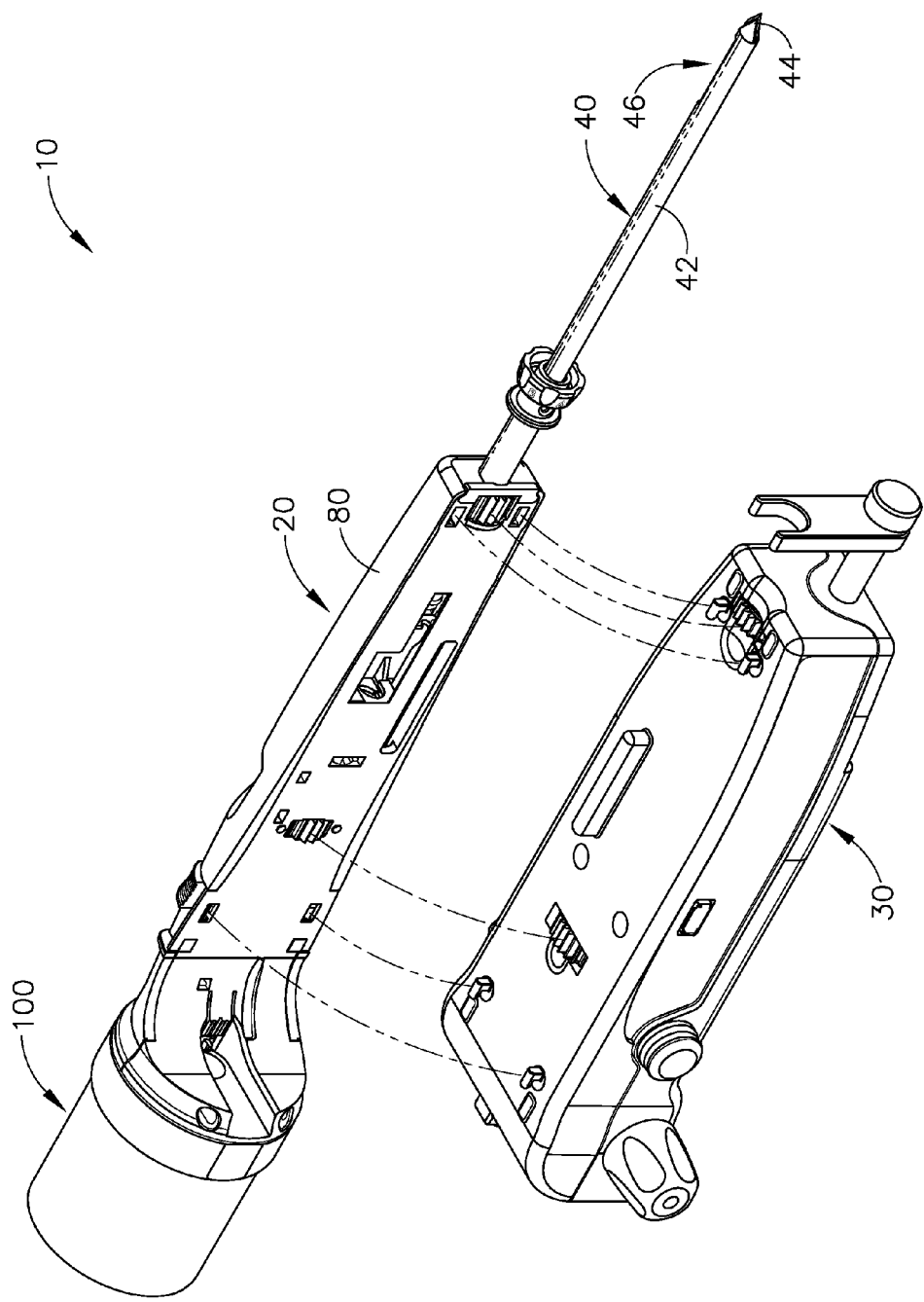
FIG. 2 depicts a perspective view of an exemplary biopsy device showing an exemplary probe decoupled from an exemplary holster.

FIG. 1 shows an exemplary biopsy device (10). Biopsy device (10) comprises a probe (20) and a holster (30). Probe (20) has a needle (40) that extends distally from a casing (80) of probe (20) and is insertable into a patient's tissue to obtain tissue samples, as will be described below. Biopsy device (10) further comprises a tissue sample holder (100) into which the tissue samples are deposited. By way of example only, probe (20) may be a disposable component and holster (30) may be a reusable component to which probe (20) may be coupled, as shown in FIG. 2. Use of the term "holster" herein should not be read as requiring any portion of probe (20) to be inserted into any portion of holster (30). Indeed, in one configuration for biopsy device (10), probe (20) may simply be positioned atop holster (30). Alternatively, a portion of probe (20) may be inserted into holster (30) to secure probe (20) to holster (30). In yet another version, a portion of holster (30) may be inserted into probe (20). Further still, probe (20) and holster (30) may be integrally formed as a single unit. In versions where probe (20) and holster (30) are separable members, a port and/or a seal may be provided on holster (30) to couple with a second port and/or a second seal on probe (20) such that the vacuum produced by a vacuum pump coupled to holster (30) may be fluidly connected to probe (20). Indeed, in one merely exemplary version, the vacuum pump induces a vacuum within needle (40) as will be described in more detail below. The vacuum pump may be coupled by vacuum tubes to appropriate ports on biopsy device (10). Other suitable structural and functional combinations for probe (20) and holster (30) will be apparent to one of ordinary skill in the art in view of the teachings herein.

II. Exemplary Probe

As described above, probe (20) has a needle (40) extending distally from probe (20) and a tissue sample holder (100) coupled to a proximal end of probe (20).

A. Exemplary Bubble Level

In certain situations, it may be desirable for a user to align or keep biopsy device (10) level during a procedure. One merely exemplary situation may occur during a MR biopsy when using a targeting grid with biopsy device (10). Merely exemplary biopsy device grids are disclosed in U.S. patent application Ser. No. 12/485,119, entitled "Biopsy Targeting Cube with Elastomeric Edges," filed Jun. 16, 2009; U.S. patent application Ser. No. 12/485,138, entitled "Biopsy Targeting Cube with Elastomeric Body," filed Jun. 16, 2009; U.S. patent application Ser. No. 12/485,168, entitled "Biopsy Targeting Cube with Malleable Members," filed Jun. 16, 2009; U.S. patent application Ser. No. 12/485,278, entitled "Biopsy Targeting Cube with Angled Interface," filed Jun. 16, 2009; and U.S. patent application Ser. No. 12/485,318, entitled "Biopsy Targeting Cube with Living Hinges," filed Jun. 16, 2009. The disclosure of each of the above-cited U.S. Patent Applications is incorporated by reference herein. When utilizing one of these exemplary grids, it may be useful to keep biopsy device (10) level to properly target a tissue lesion for sampling. For instance, by maintaining biopsy device (10) level with one of the exemplary grids, the accuracy of targeting a lesion may be increased by reducing the possibility of tilting while inserting biopsy device (10) into the patient's tissue. Accordingly, a leveling device for biopsy device (10) may be useful to the user during such situations.

Casing (80) of the present example may comprise a leveling device (86) coupled to an outer surface (82) of casing (80). In the example shown in FIG. 1, leveling device (86) is shown as a bulls eye bubble level attached to the top of outer surface (82) of casing (80), though it should be understood that the present configuration is merely exemplary. Indeed, leveling device (86) may alternatively comprise a single tubular bubble level, a pair of orthogonal tubular bubble levels, or any other suitable leveling device (86) as will be apparent to one of ordinary skill in the art in view of the teachings herein. In some situations where two orthogonal tubular bubble levels are utilized, a first tubular bubble level may be attached to a side of outer surface (82) while the second tubular bubble level may be attached to a proximal end of outer surface (82). In this configuration, the first tubular bubble level is configured to determine whether biopsy device (10) is longitudinally level and the second tubular bubble level is configured to determine whether biopsy device (10) is laterally level. Alternatively, in the version having the bulls eye bubble level shown in FIG. 1, the single bulls eye level is configured to determine whether biopsy device (10) is both longitudinally and laterally level. Furthermore, leveling device (86) may be integrated into casing (80), adhesively attached to outer surface (82), detachably coupled to outer surface (82), or coupled to casing (80) in any other suitable method as will be apparent to one of ordinary skill in the art in view of the teachings herein. In yet a further alternative, leveling device (86) may be coupled to holster (30), tissue sample holder (100) or needle (40) to indicate when biopsy device (10) is longitudinally and/or laterally level.

While some merely exemplary configurations for casing (80) have been described, other equally suitable configurations will be apparent to one of ordinary skill in the art in view of the teachings herein.

B. Exemplary Needle for Exemplary Probe

Needle (40) of the present example includes a cannula (42), a distal tip (44), and a lateral aperture (46) proximal to distal tip (44). Distal tip (44) shown in FIGS. 1-2 is configured to pierce and penetrate tissue without requiring a high amount of force or requiring an opening to be preformed in the tissue prior to insertion of distal tip (44), though it should be understood that distal tip (44) may have other suitable configurations, including a blunt tip. Distal tip (44) may comprise a blade assembly for coupling a flat blade to cannula (42), such as the one described in U.S. patent application Ser. No. 13/150,950, entitled "Needle Assembly and Blade Assembly for Biopsy Device," filed Jun. 1, 2011, the disclosure of which is incorporated by reference herein. Yet other equally suitable configurations for distal tip (44) will be apparent to those of ordinary skill in the art in view of the teachings herein.

Needle (40) of the present example is also coupled to a pair of indicators (72) shown within indicator windows (70) of casing (80). Indicators (72) may be rotatable drums having a plurality of markings, such as numbers, letters, and/or colors, to provide an indication to a user of the orientation of needle (40). In the present example, indicators (72) are coupled to gears that mesh with a complementary gear on a proximal portion of needle (40) such that when needle (40) is rotated about its longitudinal axis, either through a user using a thumbwheel or by a motor, indicators (72) then rotate as well. In one merely exemplary version, indicators (72) may be aligned and have a plurality of markings to indicate the o'clock position of lateral aperture (46). In an alternative version, indicators (72) may indicate the orientation of distal tip (44). Still further configurations for indicators (72) will be apparent to those of ordinary skill in the art in view of the teachings herein.

Needle (40) may further be divided into a first lumen (94) and a second lumen (96). One such exemplary configuration for needle (40) is described in U.S. patent application Ser. No. 13/150,950, entitled "Needle Assembly and Blade Assembly for Biopsy Device," filed Jun. 1, 2011. In one version, needle (40) may be an ovular cross-sectional tube having a cut-out portion extending longitudinally from the distal end of needle (40) and terminating at a position proximal of the distal end. For example, the cut-out portion may extend longitudinally along the entire length of needle (40) or the cut-out portion may terminate at a longitudinal position less than the length of needle (40) and distal of the proximal end of needle (40). A circular cross-sectional tube may be attached where the cut-out portion was removed; the interior of the circular cross-sectional tube defining a first lumen (94) and the combination of the exterior of the circular cross-sectional tube and a partial section of needle (40) defining a second lumen (96) parallel to first lumen (94). Alternatively, a longitudinal wall (not shown) may be inserted into needle (40) and attached to the interior of needle (40). The top region of needle (40) and the longitudinal wall defining the first lumen (94) and the bottom region of needle (40) and the longitudinal wall defining the second lumen (96). A plurality of openings may be formed within the longitudinal wall or the circular cross-sectional tube to permit fluid communication between first lumen (94) and second lumen (96). Still other suitable configurations for needle (40) having a first lumen (94) and a second lumen (96) will be apparent to one of ordinary skill in the art in view of the teachings herein.

Lateral aperture (46) is located proximally of distal tip (44) and is sized to receive tissue when needle (40) is inserted into the tissue of a patient. A tubular cutter (90) is disposed within first lumen (94) of needle (40) and is operable to rotate and/or translate relative to needle (40) to sever tissue protruding through lateral aperture (46). Tubular cutter (90), as partially shown in FIG. 3, comprises a sharp distal end and defines a cutter lumen (98) therein. In the present example, tubular cutter (90) is actuated by a motor, though it should be understood that tubular cutter (90) may be actuated by a variety of mechanical or electromechanical components, such as a pneumatic system, a spring-loaded system, or any other suitable component. Tubular cutter (90) is configured to actuate between a distal-most position, in which tubular cutter (90) substantially blocks access through lateral aperture (46) resulting in a "closed" lateral aperture (46), and a proximal-most position, in which a distal end of tubular cutter (90) is proximal to a proximal edge of lateral aperture (46) resulting in an "open" lateral aperture (46). Thus, when lateral aperture (46) is in an "open" position, tissue may be drawn through lateral aperture (46) and into cannula (42), thereby permitting tubular cutter (90) to be advanced distally to sever a tissue sample with the sharp distal end. Additionally, while lateral aperture (46) is in an "open" position, items from within cannula (42) or elsewhere within biopsy device (10) may be expelled out through lateral aperture (46) and into the tissue of a patient or into a cavity formed after a tissue sample has been removed. Merely exemplary items that may be expelled through lateral aperture (46) include medication, saline, portions of other medical devices, biopsy site markers, or any other suitable item as will be apparent to one of ordinary skill in the art in view of the teachings herein.

When biopsy device (10) is operated, second lumen (96) may be configured to selectively provide atmospheric air, vacuum and/or saline to cutter lumen (98). The plurality of openings described above may be arranged such that at least one opening is located at a longitudinal position that is distal to the distal edge of lateral aperture (46) such that cutter lumen (98), first lumen (94), and second lumen (96) remain in fluid communication even when tubular cutter (90) is advanced to the distal-most position. In one merely exemplary operational mode, when a tissue sample is severed by tubular cutter (90), a vacuum may be applied to cutter lumen (98) while atmospheric air is provided through a vent fluidly coupled to first lumen (94) and/or second lumen (96). The combination of vacuum on one side of the tissue sample and atmospheric air on the other may cooperatively urge the tissue sample proximally through tubular cutter (90) and towards tissue sample holder (100). Alternatively, when no tissue samples are present within needle (40), saline may be flushed through cutter lumen (98), first lumen (94), and second lumen (96) to clear any debris within. A valve assembly may be provided in probe (20) or holster (30) to selectively change between the various configurations. One such valve assembly may be constructed in accordance with at least some of the teachings of U.S. Pub. No. 2010/0317997, entitled "Tetherless Biopsy Device with Reusable Portion," published Dec. 16, 2010; in accordance with the teachings of U.S. patent application Ser. No. 12/953,715, entitled "Handheld Biopsy Device with Needle Firing," filed Nov. 24, 2010; and/or otherwise. Alternatively, in the present example, a separate control module can be provided that has internal controls to selectively apply vacuum, saline, and/or atmospheric air. One such control module may be constructed in accordance with at least some of the teachings of U.S. Pub. No. 2010/0160817, entitled "Control Module Interface for MRI Biopsy Device," published Jun. 24, 2010. Other suitable alternative versions, features, components, configurations, and functionalities of needle (40) will be apparent to those of ordinary skill in the art in view of the teachings herein.

C. Exemplary Tissue Sample Holder

In some situations it may be useful to have access to the cutter lumen, first lumen, and/or lateral aperture of a biopsy device. As discussed above, this access may be desirable to expel items out through the lateral aperture into a patient's tissue or into a cavity formed in the tissue after excising a biopsy sample. Merely exemplary items that may be expelled include medication, saline, portions of other medical devices, biopsy site markers, or any other suitable item. In certain situations, the only accessible portion of a biopsy device may be the proximal end of the device. Accordingly, if a tissue sample holder is coupled to the proximal end of the biopsy device, access through the tissue sample holder may be useful to expel one of the above-mention items. Moreover, it may also be preferable to provide selective access through the tissue sample holder such that a vacuum can be provided prior to access to clear the biopsy device of debris. Furthermore, by providing selective access through the tissue sample holder, the user may not need to remove and reattach the tissue sample holder each time access is desired, thereby possibly preserving sterility and maintaining ease of use of the device. Accordingly, providing a chamber within the tissue sample holder through which access to the cutter lumen, first lumen, and/or lateral aperture is possible may be useful to a user of a biopsy device.

Figure 3:
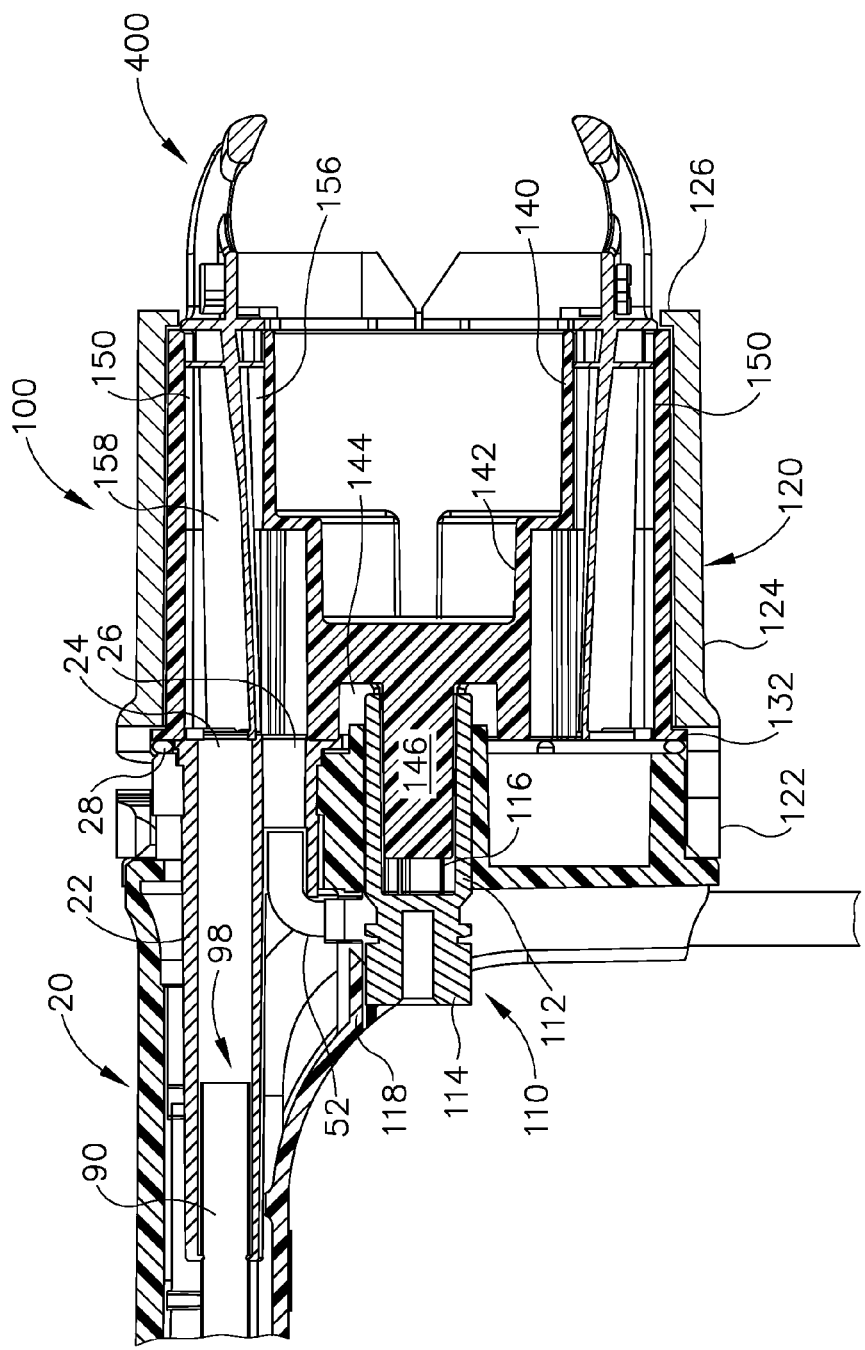
FIG. 3 depicts a cross-sectional view of an exemplary tissue sample holder.

As seen in FIG. 3, an exemplary tissue sample holder (100) is detachably coupled to the proximal end of probe (20). Tissue sample holder (100) of the present example is configured to receive tissue samples that are severed by tubular cutter (90) and communicated proximally through cutter lumen (98). Probe (20) of the present example comprises a transfer member (22) in fluid communication with cutter lumen (98) within needle (40) and a vacuum line (52) coupled to a vacuum pump. In the present example, transfer member (22) has a needle aperture (24) and a vacuum aperture (26). Transfer member (22) is configured to selectively connect needle (40) to a tray portion (158) of a selected chamber (150) and selectively connect vacuum line (52) to a vacuum portion (156) of the selected chamber (150) such that vacuum line (52), selected vacuum portion (156), selected tray portion (158), and needle (40) are all in fluid communication. By way of example only, transfer member (22) may be made from a resilient material, such as rubber, synthetic rubbers (such as Neoprene), liquid silicone rubber, santoprene, or any other suitable material. Tissue sample holder (100) as shown in FIG. 3 further comprises one or more removable trays (400), an outer cover (120), and a rotatable manifold (140).

1. Exemplary Rotatable Manifold

Figure 4:
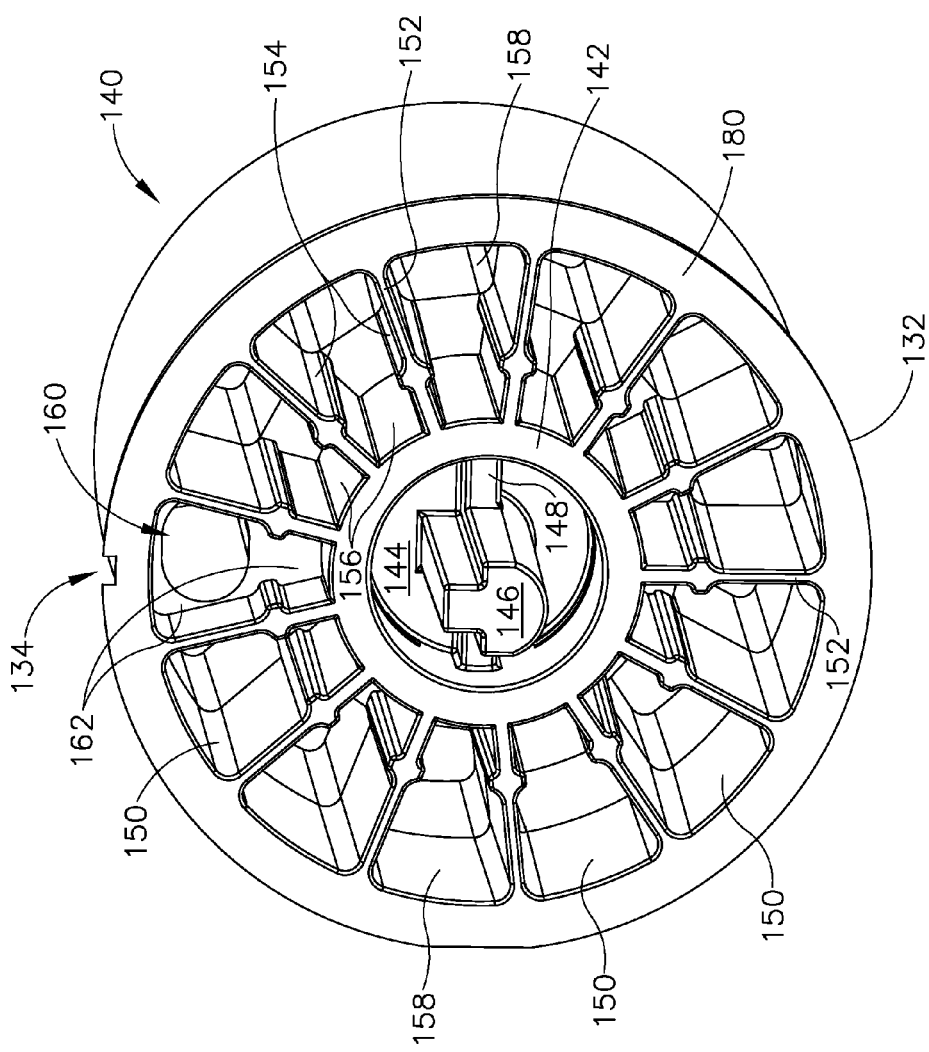
FIG. 4 depicts a perspective view of an exemplary rotatable manifold.

Referring now to FIG. 4, rotatable manifold (140) comprises a plurality of chambers (150) positioned about a central hub (142) where each of the plurality of chambers (150) extend through rotatable manifold (140). In the present example, thirteen chambers (150) are radially positioned about central hub (142) with at least one chamber configured to be an access chamber (160) and as will be described in more detail below. It should be understood that more than thirteen or less than thirteen chambers (150) may be radially positioned about central hub (142). Central hub (142) is configured to couple to a portion of probe (20) such that rotatable manifold (140) may be rotated relative to probe (20). Rotatable manifold (140) may further comprise a distal flange (132) and a complementary slot (134) formed therein, as will be described in more detail below.

Figure 5:
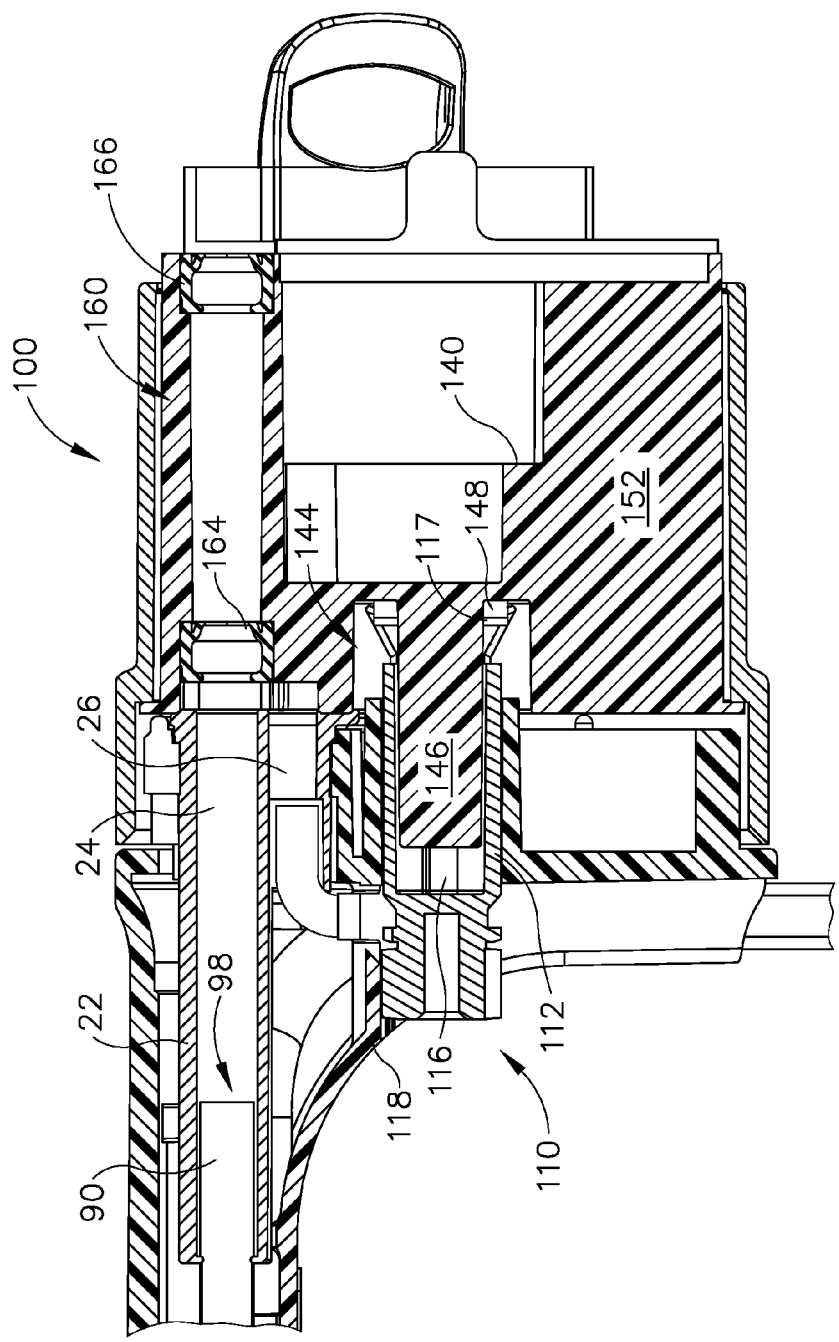
FIG. 5 depicts a cross-sectional view of an exemplary tissue sample holder having an inner valve and an outer valve and coupled to a probe.

As shown in FIG. 3, probe (20) of the present example comprises a rotation member (110) configured to be insertable into a central recess (144) of central hub (142). By way of example only, rotation member (110) comprises a shaft (112) having a proximal end and a distal end, a manifold gear (114) attached to the distal end of shaft (112), a shaft recess (116) extending distally from the proximal end, and a cross-slot (117), shown in FIG. 5, located at the proximal end of shaft (112). In the present version, shaft recess (116) is configured to receive a manifold shaft (146) and cross-slot (117) is configured to couple to a slot member (148) such that rotatable manifold (140) may be rotated when manifold gear (114) of rotation member (110) is rotated. Probe (20) further comprises a pawl (118) configured to selectively engage manifold gear (114). Pawl (118) is configured to be biased towards manifold gear (114). When probe (20) is detached from holster (30), pawl (118) actuates to engage manifold gear (114) and inhibits rotation of rotation member (110). Conversely, when probe (20) is coupled to holster (30), pawl (118) is disengaged from manifold gear (114) to permit rotation of rotation member (110). One merely exemplary configuration to disengage pawl (118) is a tab extending outwardly from holster (30).

Still referring to FIG. 3, central recess (144) is configured to receive a portion of shaft (112) while manifold shaft (146) is inserted into shaft recess (116) and cross-slot (117) is coupled to slot member (148). Pawl (118) may retain rotation member (110) in a stationary position while shaft recess (116), cross-slot (117), manifold shaft (146) and slot member (148) are aligned. As a result of this alignment, a selected chamber (150) of rotatable manifold (140) is aligned with needle aperture (24) of transfer member (22). In addition, this alignment may permit biopsy device (10) to keep track of the orientation of tissue sample holder (100) either electronically (such as with a control board and appropriate programming) or mechanically (such as with a numbered disc, drum, or other physical member with markings) even while changing between different tissue sample holders (100). With tissue sample holder (100) coupled to probe (20), rotatable member (110) is operable to rotate rotatable manifold (140) utilizing the engagement of shaft recess (116), cross-slot (117), manifold shaft (146), and slot member (148). Additionally, an alignment pin recess (not shown) may be included on the distal end of rotatable manifold (140) to engage an alignment pin extending from the proximal end of probe (20), such as that disclosed in U.S. patent application Ser. No. 13/099,497, entitled "Biopsy Device with Manifold Alignment Feature and Tissue Sensor," filed May 3, 2011, the disclosure of which is incorporated by reference herein. The alignment pin may be configured to translate proximally in response to proximal movement of cutter (90) and, if rotatable manifold (140) is properly aligned, the alignment pin enters alignment pin recess. Alignment pin recess may be configured to be a longitudinal conical funnel such that if rotatable manifold (140) is slightly askew, then the proximal movement of the alignment pin may engage the sidewalls of the conical funnel to adjust the alignment of rotatable manifold (140). Of course, other equally suitable configurations for alignment pin and alignment pin recess will be apparent to those of ordinary skill in the art in view of the teachings herein.

i. Exemplary Chambers

As mentioned above, FIG. 4 depicts a plurality of chambers (150) radially positioned about central hub (142). Rotatable manifold (140) is rotatable such that each chamber (150) may be selectively aligned with needle aperture (24) and vacuum aperture (26). Chambers (150) of the present example are partial pie-shaped chambers extending substantially through rotatable manifold (140), though it should be understood that chambers (150) may have other configurations. Merely exemplary alternative chambers (150) include circular chambers, square chambers, triangular chambers, or any other suitable shape. Chambers (150) may also extend only partially through rotatable manifold (140) instead of completely through. Moreover, as in the present example, a portion of chamber (150) may extend completely through rotatable manifold (140) while a second portion does not. Chambers (150) are separated by a plurality of walls (152) such that each chamber (150) is substantially in fluid isolation relative to every other chamber (150). Each wall (152) comprises a pair of ledges (154) extending longitudinally along each chamber (150) and outwardly from wall (152). Ledges (154) are configured to support tissue sample containers (450), shown in FIGS. 3 and 9, of removable trays (400), as will be described later herein. The interiors of chambers (150) are divided into a vacuum portion (156) and a tray portion (158). Vacuum portion (156) is defined by the portion of chamber (150) located between central hub (142) and ledges (154). Tray portion (158) is defined by the portion of chamber (150) located between ledges (154) and an outer edge (180) of rotatable manifold (140).

In one merely alternative version, a wall may be inserted into each chamber (150) where ledges (154) protrude, thereby physically defining vacuum portion (156) and tray portion (158). In yet a further alternative, the wall may be integrally formed in rotatable manifold (140). The wall in this version may include a plurality of openings to permit fluid communication between tray portion (158) and vacuum portion (156). In yet a further version, a proximal wall may be formed at the proximal end of each chamber (150). A length of vacuum portion (156) may extend vertically into this proximal wall and the proximal wall may comprise a plurality of openings such that the proximal end of tray portion (158) is in fluid communication with vacuum portion (156). Vacuum portion (156) may also be omitted entirely or vacuum portion (156) may be located elsewhere on rotatable manifold (140).

Further still, in another version, rotatable manifold (140) may include a disc with a plurality of radially outwardly extending chambers (150). Further still, rotatable manifold (140) may instead be a translatable linear manifold that includes vertical and/or horizontal chambers (150), or, in yet a further version, a matrix of chambers (150) may be provided in a rectangular manifold. Of course other configurations for rotatable manifold (140) will be apparent to one of ordinary skill in the art in view of the teachings herein.

ii. Exemplary Access Chamber Configurations

At least one chamber of the plurality of chambers (150) is configured to be an access chamber (160). Access chamber (160) of the present example is configured differently from the other chambers (150), though it should be understood that this is merely optional. In the present example, access chamber (160) comprises a tubular chamber extending through rotatable manifold (140) and having recessed portions (162) at the distal and proximal ends that are configured to receive valve members (164, 166). In one merely exemplary version shown in FIG. 5, access chamber (160) comprises an inner valve (164) and an outer valve (166). Inner valve (164) is located substantially at the distal end of access chamber (160) and outer valve (166) is located substantially at the proximal end of access chamber (160). Inner valve (164) may be configured to be a variety of different valve types, including duckbill valves, domed valves, cross-slit valves, domed cross-slit valves, and/or any other suitable valve or combination of valves as will be apparent to one of ordinary skill in the art in view of the teachings herein. Inner valve (164) and/or recessed portion (162) may further be configured to have a recessed distal face such that needle aperture (24) and vacuum aperture (26) of transfer member (22) may be in direct fluid communication distally of inner valve (164) when access chamber (160) is aligned with transfer member (22). In this alignment, if a vacuum is applied by a vacuum pump, a vacuum path is formed from first lumen (94), through cutter lumen (98), through needle aperture (24) of transfer member (22), and through vacuum aperture (26) to the vacuum pump. Accordingly, when the vacuum pump is activated and access chamber (160) is so aligned, first lumen (94), cutter lumen (98), needle aperture (24) and vacuum aperture (26) may be cleared of any debris while inner valve (164) isolates access chamber (160) from the vacuum. Additionally, saline, a combination of saline and vacuum, a medicinal drug, or any other suitable fluid may be applied along the same path while access chamber (160) is fluidly isolated.

Outer valve (166) may be the same type of valve as inner valve (164) or outer valve (166) may be any other type of valve different from inner valve (164). Outer valve (166) provides a second, exterior seal for access chamber (160) to prevent objects from accidentally entering or exiting access chamber (160). An item may be inserted through outer and inner valves (166, 164), through needle aperture (24), through cutter lumen (98), through first lumen (94), and, optionally, out lateral aperture (46) to access the cavity where a biopsy sample was taken from. With this version, access to the biopsy site is permissible through the proximal end of biopsy device (10) while needle (40) is still inserted within the patient.

Figure 6:
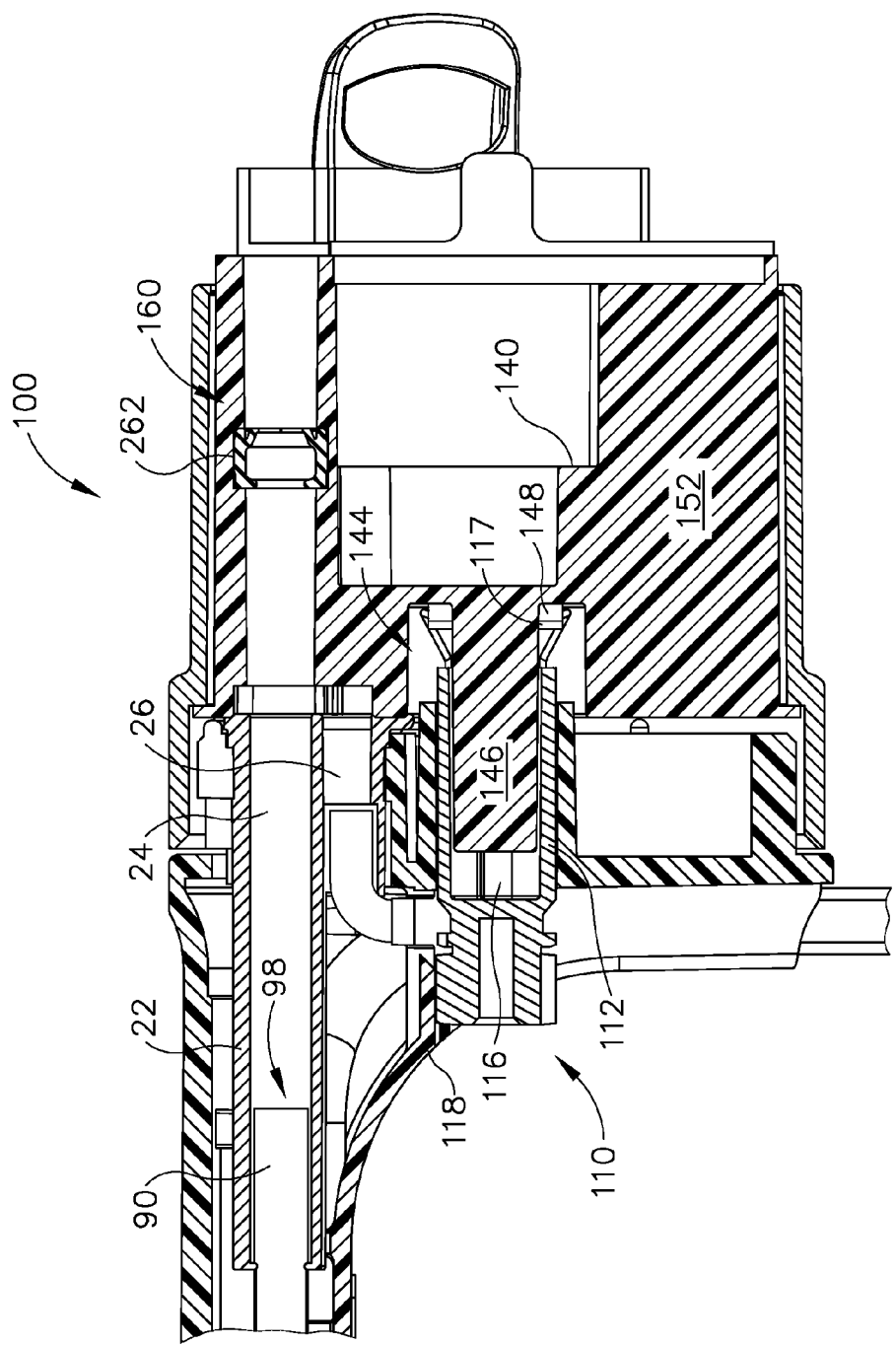
FIG. 6 depicts a cross-sectional view of an exemplary alternative tissue sample holder having a single valve.

In an alternative version, shown in FIG. 6 access chamber (260) may comprise a single valve (262) located at a point within access chamber (260). For example, single valve (262) may be located at the longitudinal midpoint of access chamber (260). Single valve (262) may be configured to be a variety of different valve types, including duckbill valves, domed valves, cross-slit valves, domed cross-slit valves, and/or any other suitable valve or combination of valves as will be apparent to one of ordinary skill in the art in view of the teachings herein. With single valve (262) in place, a vacuum may be drawn by the vacuum pump through needle (40) while access chamber (260) is aligned with needle aperture (24) without losing much, if any, vacuum through access chamber (260). Accordingly, cutter lumen (98), first lumen (94), and second lumen (96) of needle (40) may be cleared of debris by the application of vacuum while access chamber (260) is aligned. An item may be inserted through single valve (262), through needle aperture (24), through cutter lumen (98), through first lumen (94) and, if necessary, out lateral aperture (46) to access the cavity where a biopsy sample was taken from. Thus, access to the biopsy site is also permissible while needle (40) is still inserted within the patient utilizing this alternative version. Of course, with the aforementioned seals (164, 166, 262) may be overmolded or integrally formed for each access chambers (160, 260).

Figure 7:
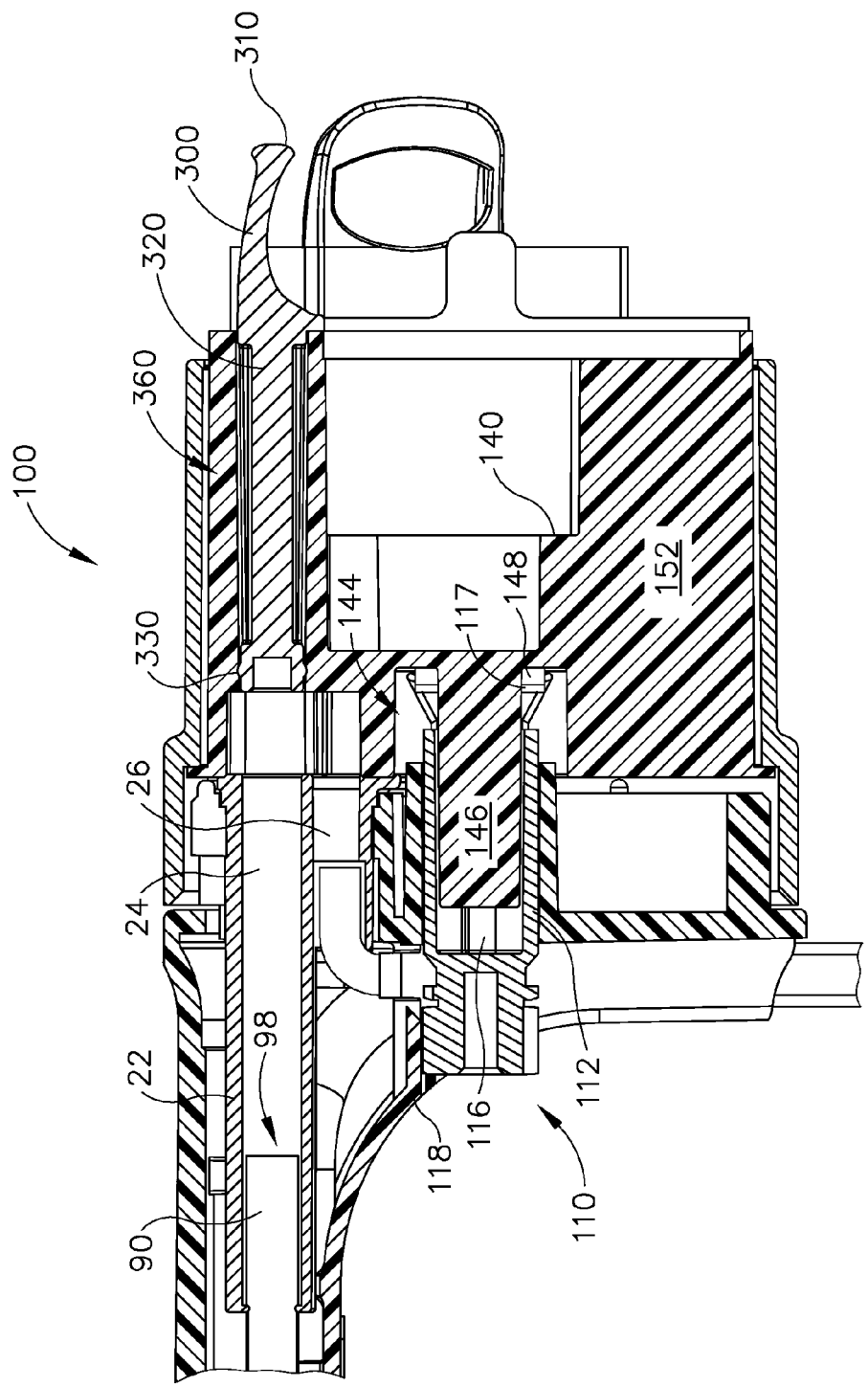
FIG. 7 depicts a cross-sectional view of yet another exemplary tissue sample holder and an exemplary removable plug.

Still yet another version for access chamber (360) includes a removable plug (300) as shown in FIG. 7. In this version, access chamber (360) is a chamber substantially similar to access chamber (260) except single valve (262) is omitted. Exemplary removable plug (300) comprises a handle (310) and a shaft (320). Shaft (320) is sized to be insertable into substantially the entire length of access chamber (360). Alternatively, shaft (320) may extend less than the entire length of access chamber (360). Shaft (320) may further include at least one annular sealing member (330) disposed about shaft (320) at a point distal of handle (310). In the example shown in FIG. 7, removable plug (300) has a resilient annular sealing member (330) disposed about shaft (320) at the distal end of shaft (320). Shaft (320) and resilient annular sealing member (330) may be made of a resilient material, such as low-density polyethylene (LDPE). A plurality of resilient annular sealing members (330) may be disposed about shaft (320) at a plurality of points distal of handle (310). Annular sealing member (330) may alternatively be a flexible member that tapers as it extends outwardly from shaft (320) to form a wiper-type seal. As with other components described herein, shaft (320) and annular sealing member (330) may have any other suitable configuration as will be apparent to one of ordinary skill in the art in view of the teachings herein. Handle (310) is shown as a tab extending from shaft (320) having a flared portion at the proximal end. When removable plug (300) is inserted into access chamber (360), removable plug (300) substantially seals access chamber (360), thereby inhibiting fluid flow in to or out of biopsy device (10) through access chamber (360). With removable plug (300) inserted, a vacuum may be drawn by the vacuum pump while access chamber (360) is aligned with needle aperture (24) without losing much, if any, vacuum through access chamber (360). Accordingly vacuum aperture (26), needle aperture (24), cutter lumen (98), first lumen (94), and/or second lumen (96) may be cleared of debris by the application of vacuum prior to accessing the tissue through lateral aperture (42) through access chamber (360).

Figure 8:
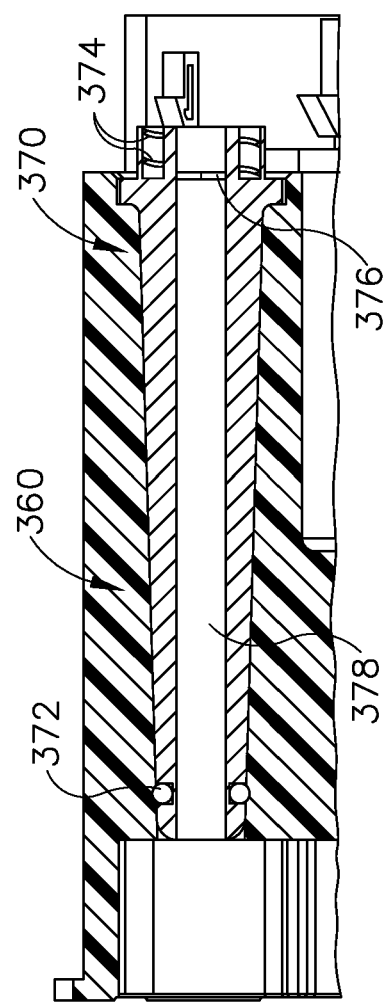
FIG. 8 depicts a partial cross-sectional view of the tissue sample holder of FIG. 7 with an exemplary luer check valve.

A luer check valve (370) may alternatively be inserted into access chamber (360), as shown in FIG. 8. Luer check valve (370) of the present example comprises a longitudinal passage (378), a seal (372) located substantially at a proximal end of luer check valve (370), a luer lock connector (374) at a distal end of the luer check valve (370), and a valve (376) disposed within longitudinal passage (378). Seal (372) is shown as a rubber or silicone o-ring seal that may prevent fluid from communicating proximally of seal (372) when luer check valve (370) is inserted into access chamber (360). Luer lock connector (374) comprises a threaded portion for coupling to a complementary luer fitting. Valve (376) is disposed distally of luer lock connector (374) and is configured to substantially prevent fluids from entering or exiting through luer check valve (370) without applying some force to the fluid. When luer check valve (370) is inserted into access chamber (360), a vacuum may be drawn by the vacuum pump while access chamber (360) is aligned with needle aperture (24) without losing much, if any, vacuum through access chamber (360). Accordingly vacuum aperture (26), needle aperture (24), cutter lumen (98), first lumen (94), and/or second lumen (96) may be cleared of debris by the application of vacuum prior to coupling a syringe or other item via luer lock connector (374). By way of example only, when a syringe is coupled to luer lock connector (374), a medicament contained within the syringe may be forced past valve (376) by depressing a plunger of the syringe. If needle aperture (24) is open to the tissue, the medicament may be applied to the tissue without removing biopsy device (10). It should be understood that items other than medicaments may be injected to the tissue, including contrast dyes, saline, gels, or other suitable items that may be used as will be apparent to one of ordinary skill in the art in view of the teachings herein. Of course, luer check valve (370) may alternatively be integrated into rotatable manifold (140). Further still, luer check valve (370) may include a spring loaded luer valve. As with other components described herein, luer check valve (370) will be apparent to one of ordinary skill in the art in view of the teachings herein.

2. Exemplary Removable Trays

Figure 9:
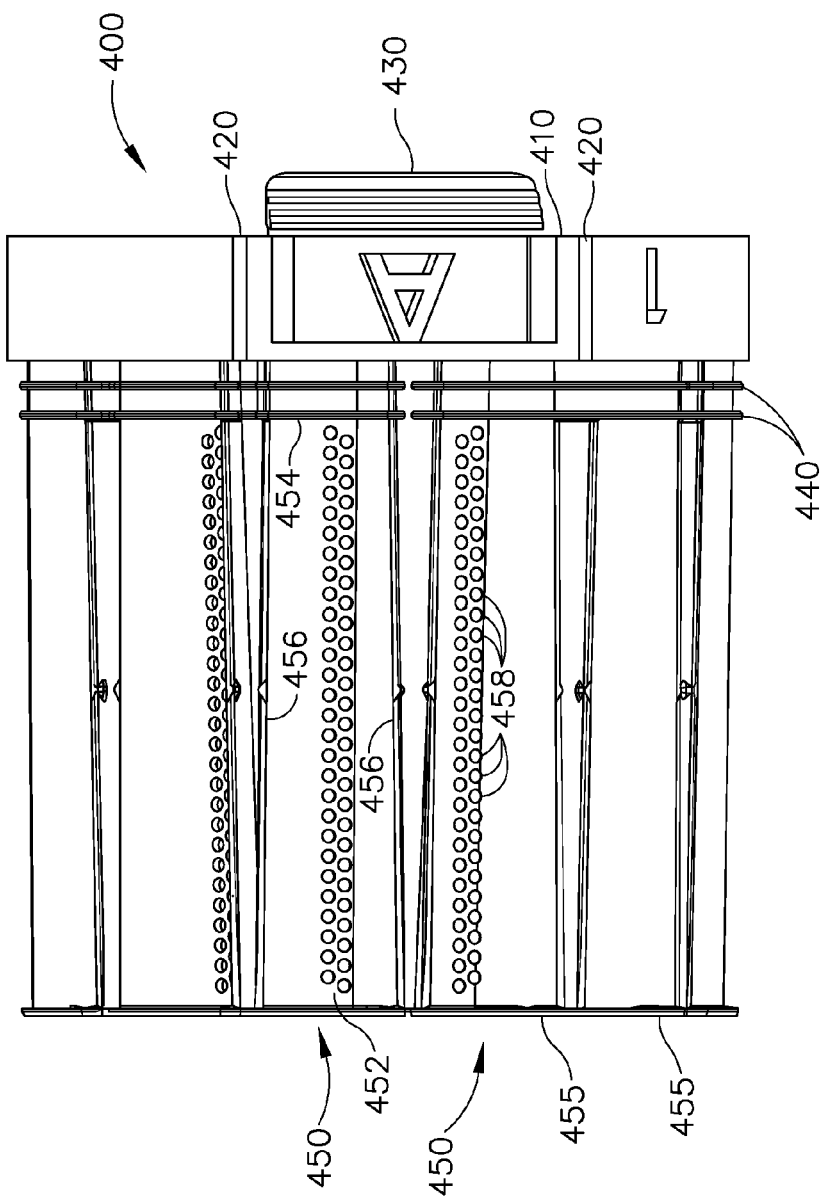
FIG. 9 depicts a top view of an exemplary tray for use with a rotatable manifold of a tissue sample holder.

One or more removable trays (400), shown in FIG. 9, are configured to permit a user to remove severed tissue samples from tissue sample holder (100) without having to decouple tissue sample holder (100) from probe (20). Each tray (400) comprises a main portion (410) and at least one tissue sample container (450). Each tray (400) may be rigid, and may be preformed to correspond to the generally arcuate configuration of rotatable manifold (140), or, alternatively, trays (400) may be formed of a flexible material, such that trays (400) may be bent or deformed to conform to the configuration of rotatable manifold (140). Further still, main portion (410) may be formed of a rigid material and coupled to a flexible material forming the at least one tissue sample container (450). Conversely, the at least one tissue sample container (450) may be formed of a rigid material while the main portion (410) comprises a flexible material. In the example shown in FIG. 9, each tray (400) comprises a main portion (410) and six tissue sample containers (450), though it should be understood that any number of tissue sample containers (450) may be used. Main portion (410) of the present example comprises one or more joints (420), such as living hinges, such that parts of main portion (410) may bend or flex at joints (420). As shown in FIG. 9, each main portion (410) of trays (400) has two living hinge joints (420). Main portion (410) further comprises a handle (430) for a user to grip and maneuver tray (400). Handle (430) may be constructed of a rigid material to not flex when gripped by a user carrying tray (400), and handle (430) may be located at the midpoint of main portion (410) of each tray (400).

Each tissue sample container (450) of the present example has a base portion (452), a proximal end wall (454), a distal end wiper wall (455), and a pair of container sidewalls (456), defining a tissue sample container (450). Tissue sample containers (450) may be integrally formed with main portion (410), or tissue sample containers (450) may be mechanically or chemically bonded to main portion (410). Distal end wiper wall (455) is sized to substantially fill the area of each chamber (150) such that when tissue sample container (450) is removed from rotatable manifold (140), distal end wiper wall (455) wipes bits of tissue off the walls of rotatable manifold (140). In the example shown, a plurality of offset members (440) offset proximal end walls (454) from main portion (410), though it should be understood that this is merely optional and proximal end walls (454) may be directly coupled to main portion (410). Plurality of offset members (440) may include wiper blade type seals and may aid the sealing of the tissue sample container (450) when inserted into the rotatable manifold (140). By way of example only, each tissue sample container (450) is configured to receive a single tissue sample severed by tubular cutter (90). Alternatively, tissue sample containers (450) may be configured such that each tissue sample container (450) may hold more than one tissue sample. Tissue sample containers (450) are configured to be insertable into chambers (150) of rotatable manifold (140) for use with biopsy device (10). In the example shown, tissue sample containers (450) are inserted through the proximal end of rotatable manifold (140) into tray portion (158) and are located atop ledges (154). Base portion (452) has a plurality of openings (458) permitting fluid communication through tissue sample container (450) into vacuum portion (156) of chamber (150). Accordingly, when tissue sample containers (450) are inserted into chambers (150), first lumen (94), cutter lumen (98), and needle aperture (24) may be in fluid communication with vacuum line (52) through tissue sample container (450), openings (458), vacuum portion (156) and vacuum aperture (26). Thus, once a tissue sample is severed by tubular cutter (90), the tissue sample may be transported proximally by vacuum pressure produced by the vacuum pump until the tissue sample is within tissue sample container (450). After the tissue sample is stored within a tissue sample container (450), rotatable manifold (140) may be rotated by rotating member (110) to align a new tissue sample container (450) with needle (40).

Each tray (400) may further comprise one or more types of markings or other indicia to distinguish one tissue sample container (450) from another tissue sample container (450). For instance, a number or other distinguishing marking may be provided on or near each tissue sample container (450), such as in relief form, in recessed form, or otherwise. In the example shown, a number of distinguishing marks are provided on main portion (410) proximal to each tissue sample container (450). In another embodiment, a radiopaque marker may be provided on or near each tissue sample container (450). For instance, an entire tray (400) that is carrying one or more tissue samples may be placed under X-ray for evaluation, and the radiopaque marker associated with each tissue sample container (450) (and accordingly, associated with a corresponding tissue sample), may be visible in the image obtained using X-ray. In other words, the tissue samples may not need to be removed from trays (400) in order to take an X-ray or radiograph image of the tissue samples. Furthermore, trays (400) may be dropped directly into formalin or any other liquid with the tissue samples still contained within tissue sample containers (450). Other structures and techniques that may be used with trays (400) as will be apparent to those of ordinary skill in the art in view of the teachings herein.

3. Exemplary Outer Cover

An outer cover (120) may also be provided with tissue sample holder (100), as shown in FIG. 3. Outer cover (120) comprises a distal coupling section (122), a hollow cylindrical body (124), and an inwardly extending proximal lip (126). Proximal lip (126) extends radially inwardly to substantially restrict rotatable manifold (140) from moving proximally along the longitudinal axis away from probe (20) when tissue sample holder (100) is coupled to probe (20). Distal coupling section (122) is configured to couple to a proximal end of probe (20). Merely exemplary coupling configurations include frictional fit, tab and slot, clamps, clips, screws, bolts, integral threading, or any other suitable coupling mechanism as will be apparent to one of ordinary skill in the art in view of the teachings herein. Additionally, a seal (28) may be provided on the proximal end of probe (20) that may aid in sealing outer cover (120) and/or rotatable manifold (140) when coupled to the proximal end of probe (20). Seal (28) of the present example comprises a rubber o-ring seal, but other equally suitable seals, including disc-type seals or silicone caulk, may be used for seal (28). Hollow cylindrical body (124) is sized such that rotatable manifold (140) can rotate within hollow cylindrical body (124) between proximal lip (126) and distal coupling section (122) while outer cover (120) is couple to probe (20). Distal coupling section (122) may further comprise a tab extending inward, and rotatable manifold (140) may comprise a complementary slot (134) formed in the distal flange (132) such that the tab may be inserted through slot (134) when inserting rotatable manifold (140) into outer cover (120). Distal flange (132) of rotatable manifold (140) substantially restricts rotatable manifold (140) from moving distally along the longitudinal axis when the tab and slot (134) are not aligned. Accordingly, it will be appreciated that distal flange (132), the tab, and proximal lip (126) cooperatively retain rotatable manifold (140) within outer cover (120) by restricting longitudinal movement of rotatable manifold (140) while still permitting rotational movement. Outer cover (120) may be made of a transparent material or a translucent material such that rotatable manifold (140) may be seen within. In such a situation, rotatable manifold may have a plurality of markings on the exterior of rotatable manifold to indicate each chamber (150, 160) of rotatable manifold, or, in one alternative, only access chamber (160) may have a corresponding marking on rotatable manifold (140). In yet a further alternative, outer cover (120) may be an opaque material.

In yet a further version, proximal lip (126) may be omitted and a pair of snap bosses (not shown) may be formed on a proximal end of rotatable manifold (140). The snap bosses extend radially outward from rotatable manifold (140) such that outer cover cannot translate proximally past the snap bosses. Such snap bosses may be located approximately 180 degrees apart from each other on rotatable manifold (140), or such snap bosses may be at any other suitable location on rotatable manifold (140), including from one degree to 180 degrees, inclusive. Furthermore, a single snap boss may be provided or, in other instances, more than two snap bosses may be provided. Of course other equally suitable configurations for outer cover (120) and rotatable manifold (140) will be apparent to one of ordinary skill in the art in view of the teachings herein.

While various exemplary versions for tissue sample holder (100) have been described, still other suitable ways in which tissue sample holder (100) may be constructed and operable will be apparent to those of ordinary skill in the art in view of the teachings herein.

III. Exemplary Marker Applier

Figure 10:
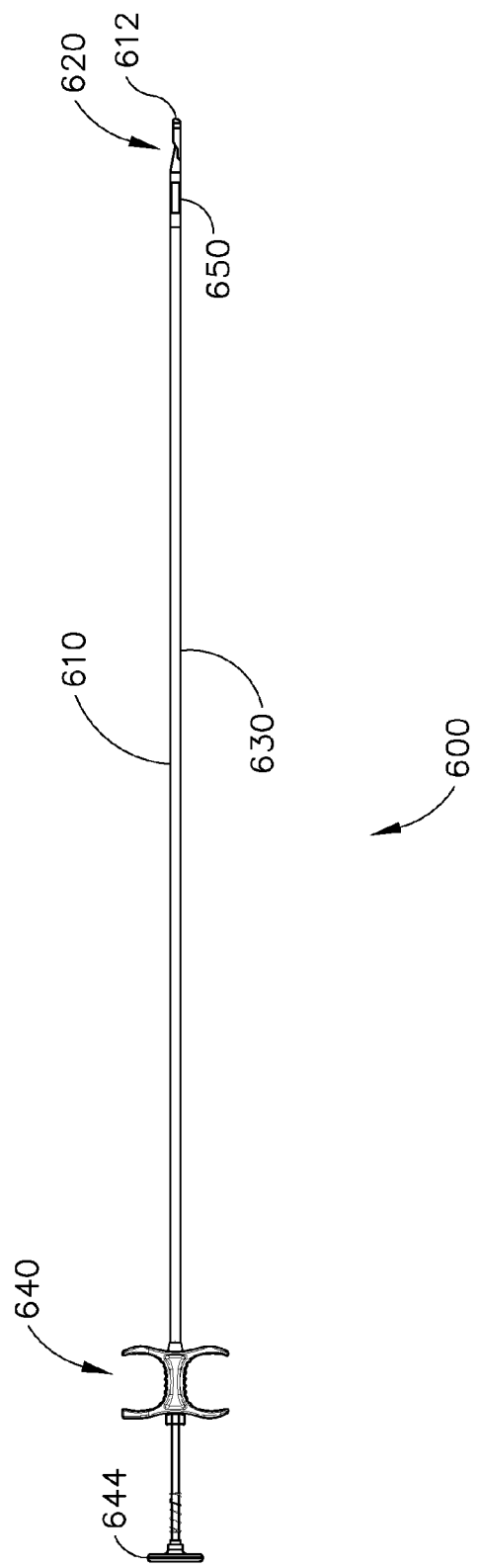
FIG. 10 depicts a side view of an exemplary marker deployment tool.

As shown in FIG. 10, an exemplary marker deployment tool (600) comprises a marker cannula (610) having a distal end (612) and a lateral deployment aperture (620). A biopsy site marker (650) is slidably disposed within marker cannula (610). Marker deployment tool (600) further comprises a push rod (630) having a distal end located proximal of biopsy site marker (650). Push rod (630) is also slidably disposed in marker cannula (610) and is operable to push biopsy site marker (650) out through the lateral deployment aperture (620), as shown in FIG. 10. Some merely exemplary marker deployment tools include the MAMMOMARK™, MICROMARK®, and CORMARK™ brand devices from Devicor Medical Products, Inc. of Cincinnati, Ohio.

A grip (640) may be coupled to marker cannula (610) and a plunger (644) may be coupled to push rod (630) such that marker deployment tool (600) may be manipulated by a single hand of a user to deploy biopsy site marker (650). For marker deployment tools (600) having a lateral deployment aperture (620), it may be necessary to include a ramp-like structure at or near the distal end of marker cannula (610) to redirect biopsy site marker (650) out lateral deployment aperture (620). In instances where a relatively flexible marker deployment tool (600) is necessary, marker cannula (610) and push rod (630) may be constructed of relatively flexible materials. Alternatively, marker cannula (610) and push rod (630) may be constructed of relatively stiff materials. Furthermore, marker cannula (610) and push rod (630) may be constructed partially of relatively flexible materials and partially of relatively stiff materials. Further still, it may be desirable for push rod (630) to be constructed of a relatively stiff material that may also be bent laterally. One exemplary material may comprise a shape memory material, such as nitinol. It should be understood that while the present disclosure describes the deployment of a biopsy site marker (650), other items may be used with marker deployment tool (600), including, but not limited to, radioactive dyes or items, medicinal items (liquid, semi-solid, or solid), and/or any other item. Other various versions and adaptations for marker deployment tool (600) will be apparent to one of ordinary skill in the art in view of the teachings herein.

A. Exemplary Scalloped Tip

In some situations, manufacturing variations create push rods of marker deployment tools of differing sizes. On occasions where the push rod is slightly longer than expected, the push rod may be redirected by the ramp at the distal end of the cannula and protrude out the lateral deployment aperture when the plunger is completely depressed. While this may not necessarily be an issue for some users, on occasion, a user utilizing a marker deployment tool may continue to depress the plunger while removing the marker deployment tool from within the biopsy device. If the push rod is still extended out the lateral deployment aperture, the biopsy device's lateral aperture and/or tubular cutter may sever a portion of the push rod when the user is removing the marker deployment tool. Accordingly, it may be useful to provide a way of limiting the tendency for the push rod to protrude out of the lateral deployment aperture, thereby reducing the likelihood of severing the push rod, or, at least decreasing the size of any portion of the push rod that is severed.

Figure 11:
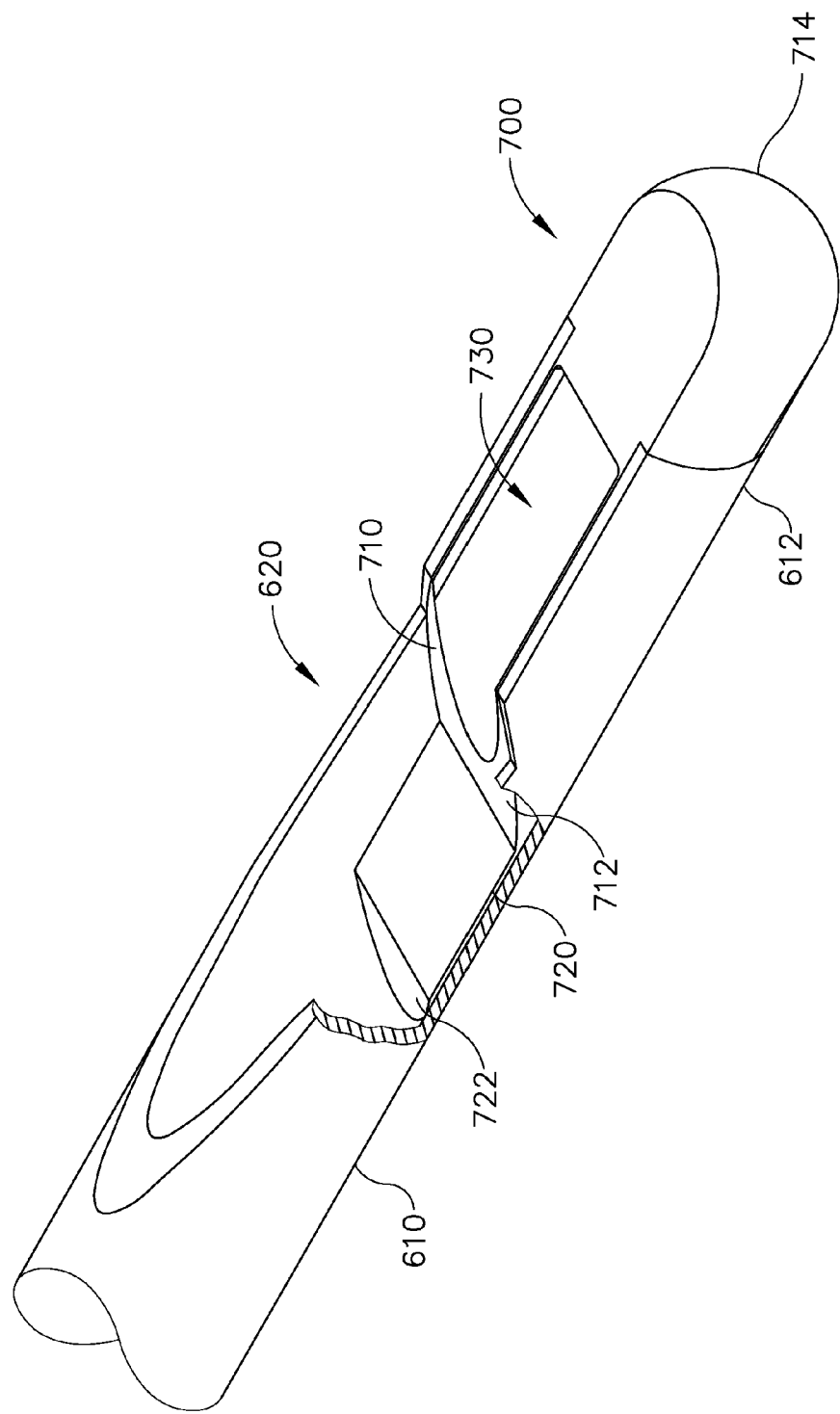
FIG. 11 depicts an enlarged perspective view of an exemplary scalloped tip of the exemplary marker deployment tool of FIG. 10.

Referring to FIGS. 10-11, a scalloped tip (700) is coupled to distal end (612) of cannula (610). Scalloped tip (700) can be a molded or cast component, and scalloped tip (700) may comprise a distal tip (714), a ramp (710) having a ramp surface (712), and a marker engaging element (720). Ramp surface (712) aids in directing biopsy marker (650) from inside marker cannula (610) through lateral deployment aperture (620). Marker engaging element (720) may optionally be employed to retain biopsy marker (650) in marker cannula (610) until the user intends to deploy biopsy marker (650). Marker engaging element (720) of the present example is disposed within marker cannula (610) and extends along a portion of marker cannula (610) opposite to lateral deployment aperture (620) such that marker engaging element (720) reinforces the portion of marker cannula (610) where lateral deployment aperture (620) is formed. One merely exemplary benefit to this arrangement is that marker engaging element (720) can help to stiffen marker cannula (610) in the region where the wall of marker cannula (610) is cut to form lateral deployment aperture (620). As shown in FIG. 11, marker engaging element (720) extends from the proximal most portion of ramp surface (712), but does not extend proximally of the proximal-most end of lateral deployment aperture (620), though it should be understood that in other embodiments a portion of marker engaging element (720) may extend proximally of lateral deployment aperture (620). Marker engaging element (720) also comprises a tapered proximal end (722) to aid in urging biopsy marker (650) out through lateral deployment aperture (620). In one merely exemplary version, marker engaging element (720) has tapered proximal end (722) having a first incident angle of approximately 30 degrees and ramp (710) has a second incident angle of approximately 45 degrees.

Scalloped tip (700) of the present example further comprises a push rod recess (730) extending proximally from ramp surface (712). Push rod recess (730) is configured to be able to at least partially receive the distal end of push rod (630) when plunger (644) is depressed, though it should be understood that push rod (630) is not required to be insertable into push rod recess (730). In the example shown in FIG. 11, push rod recess (730) comprises a hemicylindrical longitudinal recess extending from ramp (710) such that ramp surface (712) comprises a U-shaped surface for biopsy marker (650) to be deflected off of and into the biopsy site. The longitudinal length of push rod recess (730) may be determined such that the varying-length push rods (630) resulting from variations during manufacturing will fit within push rod recess (730). One merely exemplary longitudinal length for push rod recess (730) may be approximately 0.26 inches. Push rod recess (730) may also have a vertical depth between approximately 0.03 and 0.052 inches. Furthermore, push rod (630) and push rod recess (730) may be configured to have a smaller diameter than marker cannula (610) and marker (650) such that marker (650) does not enter push rod recess (730). Of course other equally suitable dimensioning will be apparent to one of ordinary skill in the art in view of the teachings herein.

In the arrangement shown in FIGS. 10-11, when push rod (630) is distally actuated by the user depressing plunger (644), push rod (630) slides biopsy marker (650) distally within marker cannula (610). When biopsy marker (650) encounters marker engaging element (720), marker (650) is deflected to exit through lateral deployment aperture (620). As push rod (630) and marker (650) advance further distally, marker (650) is further guided out of lateral deployment aperture (620) by ramp surface (712). As push rod (630) continues to advance distally to ensure that biopsy marker (650) is deployed, push rod (630) slightly deflects off of ramp surface (712) and enters push rod recess (730). When plunger (644) is fully depressed, push rod (630) of the present example may be located at least partially within push rod recess (730), though push rod (630) may alternatively not enter push rod recess (730). Thus, even if a user continues to depress plunger (644) while removing marker deployment tool (600), only a little, if any, of push rod (630) protrudes from lateral deployment aperture (620). As will be appreciated by one of ordinary skill in the art in view of the teachings herein, when the user is removing marker deployment tool (600), push rod recess (730) decreases the possibility of a portion of push rod (630) being severed by lateral aperture (46) or tubular cutter (90) of biopsy device (10).

It should be understood, however, that push rod recess (730) may be configured in other ways as well. For instance, push rod recess (730) may be an enclosed recess within scalloped tip (700) located below lateral deployment aperture (620) such that push rod (630), if it enters push rod recess (730), does not protrude out lateral deployment aperture (620). Instead, push rod (630) enters the enclosed recess. One such configuration for this enclosed cylindrical recess may be a hemicylindrical recess in marker engaging element (720) and an enclosed cylindrical recess in ramp (710). Other configurations may include various geometrically shaped recesses to accommodate a wide variety of push rod configurations. Furthermore, scalloped tip (700) may comprise a radiopaque marker embedded within scalloped tip (700) or scalloped tip (700) may be made of a radiopaque material to aid in imaging marker deployment tool (600) while deploying marker (650). Further still, scalloped tip (700) may comprise other suitable materials to be viewable through other equally suitable imaging techniques. Of course scalloped tip (700) may be configured in any other suitable fashion as will be apparent to one of ordinary skill in view of the teachings herein.

B. Exemplary Alternative Scalloped Tip

Figure 12:
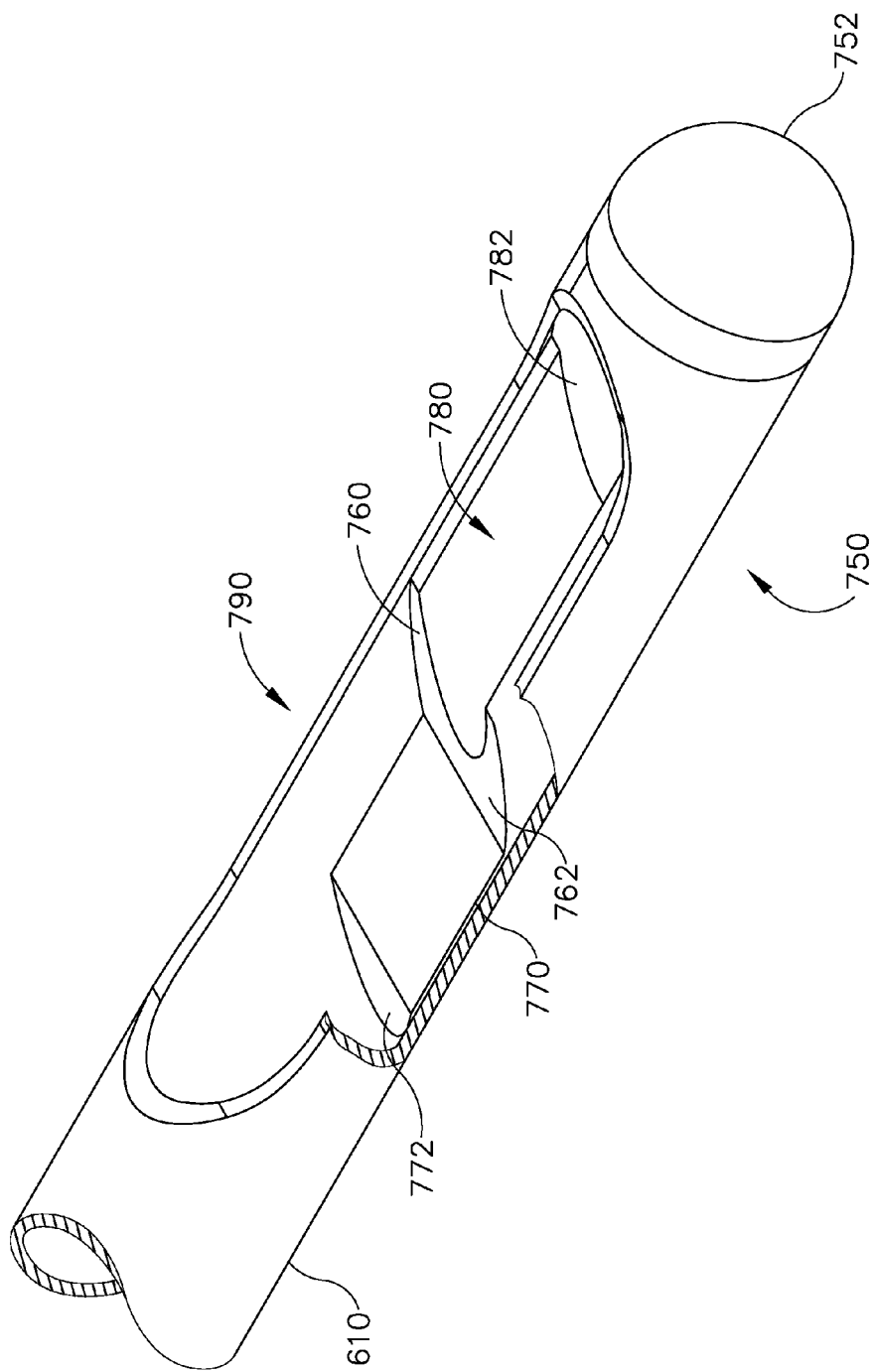
FIG. 12 depicts an enlarged perspective view of an exemplary alternative scalloped tip.

One merely exemplary alternative scalloped tip (750) is shown in FIG. 12. Alternative scalloped tip (750) can also be a molded or cast component, and alternative scalloped tip (750) of the present example comprises a distal tip (752), a ramp (760) having a ramp surface (762), and a marker engaging element (770). Ramp surface (762) aids in directing biopsy marker (650) from inside marker cannula (610) through exemplary alternative lateral deployment aperture (790). Marker engaging element (770) may optionally be employed to retain biopsy marker (650) in marker cannula (610) until the user intends to deploy biopsy marker (650), shown in FIG. 10. Marker engaging element (770) of the present example is disposed within marker cannula (610) and extends along a portion of marker cannula (610) opposite to lateral deployment aperture (790) such that marker engaging element (770) reinforces the portion of marker cannula (610) where lateral deployment aperture (790) is formed. One merely exemplary benefit to this arrangement is that marker engaging element (770) may help to stiffen marker cannula (610) in the region where the wall of marker cannula (610) is cut to form lateral deployment aperture (790). As shown in FIG. 12, marker engaging element (770) extends from the proximal most portion of ramp surface (762), but does not extend proximally of the proximal-most end of lateral deployment aperture (790), though it should be understood that in other embodiments a portion of marker engaging element (770) may extend proximally of lateral deployment aperture (790). Marker engaging element (770) also comprises a tapered proximal end (772) to aid in urging biopsy marker (650) out through lateral deployment aperture (790). In one merely exemplary configuration, marker engaging element (770) has tapered proximal end (772) having a first incident angle of approximately 30 degrees and ramp (760) has a second incident angle of approximately 45 degrees.

Alternative scalloped tip (750) of the present example further comprises a push rod recess (780) extending proximally from ramp surface (762). Push rod recess (780) is configured to be able to at least partially receive the distal end of push rod (630) when plunger (644) is depressed, though it should be understood that push rod (630) is not required to be insertable into push rod recess (780). In the example shown in FIG. 12, push rod recess (780) comprises a hemicylindrical longitudinal recess extending from ramp (760) such that ramp surface (762) comprises a U-shaped surface for biopsy marker (650) to be deflected off of and into the biopsy site. The longitudinal length of push rod recess (780) may be determined such that the varying-length push rods (630) resulting from variations during manufacturing will fit within push rod recess (780). Push rod recess (780) of the present example further comprises a distal ramp (782). Distal ramp (782) terminates at the distal end of lateral deployment aperture (790) and extends proximally into push rod recess (780). In one merely exemplary version, distal ramp (782) extends from the distal end of lateral deployment aperture (790) to a point approximately half the distance between the proximal end of push rod recess (780) and the distal end of lateral deployment aperture (790). Of course, distal ramp (782) may extend proximally to ramp (760) or to any other suitable location between ramp (760) and the distal end of lateral deployment aperture (790). Distal ramp (782) of the present example may further aid in the deployment of biopsy marker (650) by reducing the likelihood that biopsy marker (650) will catch upon the distal end of lateral deployment aperture (790). Push rod (630) and push rod recess (780) may also be configured to have a smaller diameter than marker cannula (610) and marker (650) such that marker (650) does not enter push rod recess (780). Of course other equally suitable dimensioning will be apparent to one of ordinary skill in the art in view of the teachings herein.

Similar to the arrangement shown in FIGS. 10-11, when biopsy marker (650) encounters marker engaging element (770) of the example shown in FIG. 12, marker (650) is deflected to exit through lateral deployment aperture (790). As push rod (630) and marker (650) advance further distally, marker (650) is further guided out of lateral deployment aperture (790) by ramp surface (762). As push rod (630) continues to advance distally to ensure that biopsy marker (650) is deployed, push rod (630) slightly deflects off of ramp surface (762) and enters push rod recess (780). Biopsy marker (650) may further deflect off of distal ramp (782). When plunger (644) is fully depressed, push rod (630) may be located at least partially within push rod recess (780), though push rod (630) may alternatively not enter push rod recess (780). In the example shown in FIG. 12, some push rods (630) may deflect off of distal ramp (782). Such deflection may further aid in the deployment of biopsy marker (650) out of lateral marker aperture (790). Similar to the marker deployment tool (600) of FIGS. 10-11, only a little, if any, of push rod (630) protrudes from lateral deployment aperture (790) in the present example. As will be appreciated by one of ordinary skill in the art in view of the teachings herein, when the user is removing marker deployment tool (600), push rod recess (780) decreases the possibility of a portion of push rod (630) being severed by lateral aperture (46) or tubular cutter (90) of biopsy device (10).

C. Magnetic Marker Deployment Tool Tip

While access to the patient's tissue or a cavity in the tissue may be provided through an access chamber in the tissue sample holder, in some instances the lateral aperture of the needle is located at a long distance from the access chamber. In such instances, if a marker is to be deployed into the tissue, a lengthy marker deployment tool may need to be used to reach the lateral aperture. Moreover, with small sized needles, the marker deployment tool may also be required to be a slender rod. In certain situations where the marker deployment tool is a relatively flexible tool, aligning the end of the marker deployment tool with the access chamber may become a difficult task due to the length and flexing of the tool. Accordingly, it may be desirable to have some method of assisting the user to guide the tip of the marker deployment tool to the access chamber.

Figure 13:
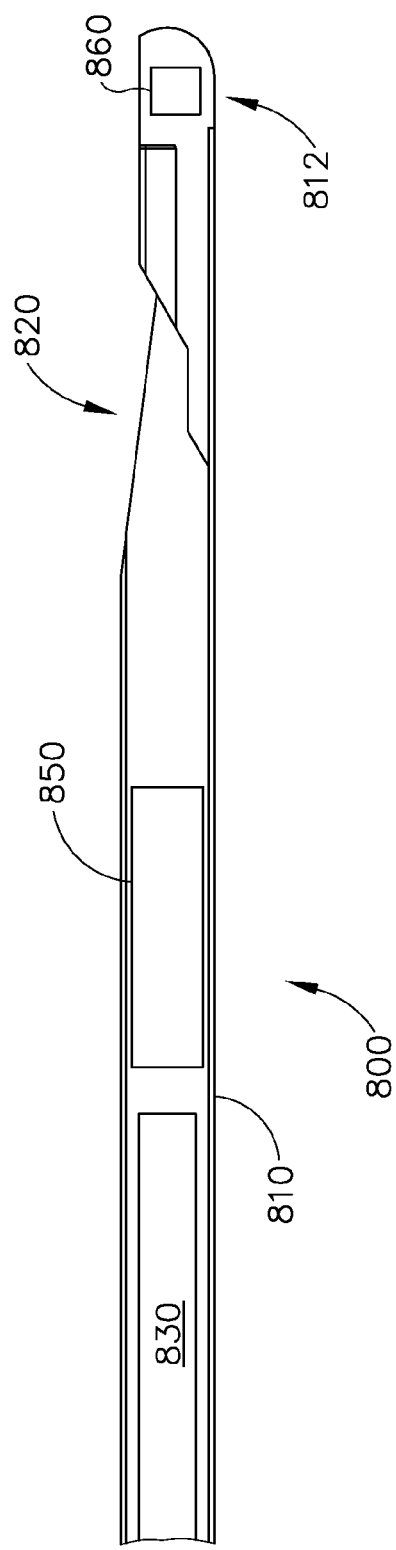
FIG. 13 depicts an alternative enlarged view of an exemplary marker deployment tool having a magnet.

An alternative marker deployment tool (800) is shown in FIG. 13. Marker deployment tool (800) comprises a marker cannula (810), a biopsy site marker (850) slidably disposed within marker cannula (810), and a push rod (830) having a distal end located proximal of biopsy site marker (850). In the present example, marker cannula (810) has a distal end (812) and a lateral deployment aperture (820), though it should be understood that these features are merely optional. For instance, marker cannula (810) may have a blunt open distal end, a sharp open distal end, a valved end, or any other suitable configuration for marker cannula (610). Push rod (830) is also slidably disposed in marker cannula (810) and is operable to push biopsy site marker (850) out through the lateral deployment aperture (820), as shown in FIG. 13. A grip may be coupled to marker cannula (810) and a plunger may be coupled to push rod (830) such that marker deployment tool (800) may be manipulated by a single hand of a user to deploy biopsy site marker (850). For marker deployment tools (800) having a lateral deployment aperture (820), a ramp-like structure, such as the scalloped tips (700, 750) described above, may be provided at or near the distal end of marker cannula (810) to redirect biopsy site marker (850) out lateral deployment aperture (820). In instances where a relatively flexible marker deployment tool (800) is necessary, marker cannula (810) and push rod (830) may be constructed of relatively flexible materials. Alternatively, it may be desirable for push rod (830) to be constructed of a relatively stiff material that may also be bent laterally. An exemplary material may comprise a shape memory material, such as nitinol. In yet other versions, push rod (830) may comprise a proximal portion and a distal portion. Proximal portion of push rod (830) may comprise a relatively stiff material while the distal portion comprises a relatively flexible material. Alternatively, the proximal portion may comprise a relatively flexible material while the distal portion comprises a relatively stiff material. Still other various versions and adaptations for marker deployment tool (800) will be apparent to one of ordinary skill in the art in view of the teachings herein.

Marker deployment tool (800) of the present example further comprises a magnet (860) disposed at or near the distal end of cannula (810). Magnet (860) may be a ferrous magnet, a neodymium magnet, a samarium-cobalt magnet, or any other suitable magnet (860) as will be apparent to one of ordinary skill in the art in view of the teachings herein. In one exemplary version, magnet (860) is embedded in distal end (812). Alternatively, magnet (860) may be adhesively attached to distal end (812). In yet a further version, magnet (860) may be embedded or adhesively coupled to marker cannula (810). Magnet (860) may also be any suitable shape, such as a sphere, disk, cylinder, bar, or any other shape. In a further version, magnet (860) may comprise a powder or a plurality of magnets that may impregnated in distal end (812). Still other equally suitable configurations for magnet (860) and marker deployment tool (800) will be apparent to one of ordinary skill in the art in view of the teachings herein.

Figure 14:
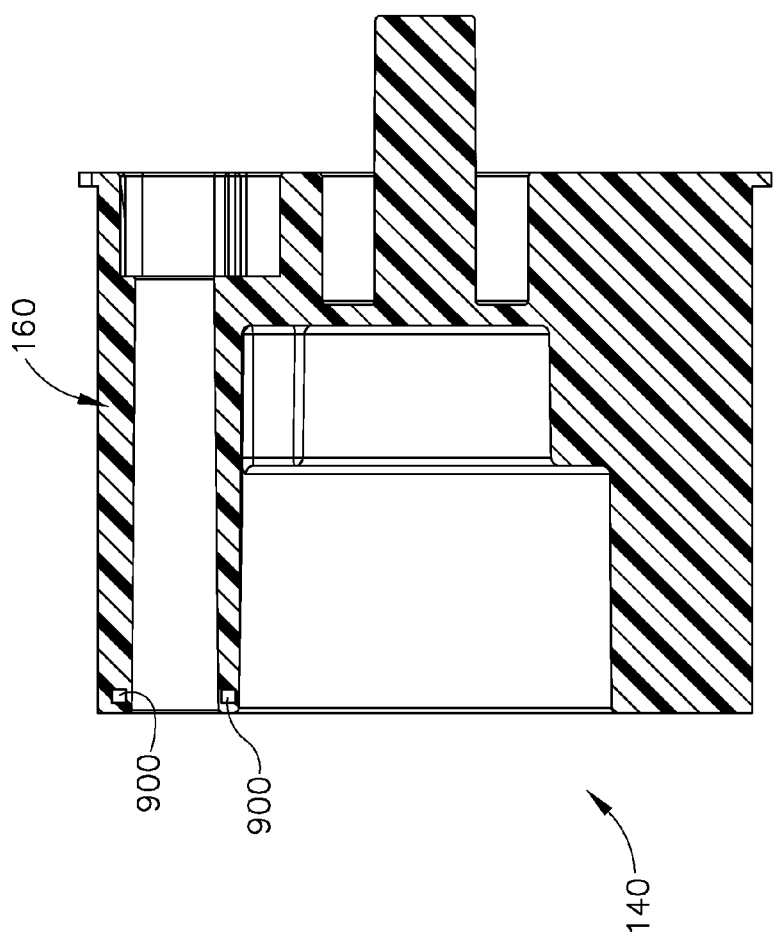
FIG. 14 depicts a rotatable manifold with complementary magnets.

A complementary magnet or magnets (900) are coupled to biopsy device (10). In one merely exemplary version shown in FIG. 14, the complementary magnets (900) may be located within rotatable manifold (140) and affixed near access chamber (160) of tissue sample holder (100), as described above. Specifically, a plurality of magnets (900) are affixed and arranged around the proximal opening of access chamber (160). In one merely exemplary version, six magnets (900) may be arranged around access chamber (160) such that access chamber (160) is the center of the ring of six magnets (900). Alternatively, an annular magnet may be used instead of a plurality of magnets. As one of ordinary skill in the art will appreciate, the ring of magnets (900) form a magnetic field that can attract magnet (860) in marker deployment tool (800) towards the ring. Alternatively, marker deployment tool (800) may comprise a magnetically attractable metal member positioned within distal end (812) of marker deployment tool (800) such that the ring of magnets (900) attracts the distal end (812). This magnetically attractable metal may comprise a powder or a plurality of metal components, such as small orbs, that may be impregnated in the distal end (812). Further still, if marker deployment tool (800) comprises a metallic marker cannula (810), then marker cannula (810) may be attracted to magnets (900). Yet a further version may include omitting magnets (900) and replacing magnets (900) with a magnetically attractable metallic annular member such that magnet (860) of marker deployment tool (800) may be attracted to the annular member. In the example shown in FIGS. 13-14, when a user may be attempting to align the tip of marker deployment tool (800), magnet (860) and magnets (900) cooperatively assist the user by magnetically guiding the tip of marker deployment tool (800) toward the opening of access chamber (160). Thus, a user may be able to single-handedly insert marker deployment tool (800) into the opening of access chamber (160) without having to grip or adjust the end of marker deployment tool (800). Still other equally suitable configurations for ring of magnets (900), magnet (860), access chamber (160), and marker deployment tool (800) will be apparent to one of ordinary skill in the art in view of the teachings herein.

While the foregoing discussion has described the complementary magnets (900) as being implemented near access chamber (160) of tissue sample holder (100), magnets (900) may be arranged at other equally suitable areas on biopsy device. For instance, in a biopsy device having a side opening for insertion of a marker deployment tool, magnets (900) may be affixed, embedded, or coupled near or around this side opening. Likewise, for a biopsy device without a proximal tissue sample holder, magnets (900) may be affixed, embedded, or coupled to a tubular cutter, such as tubular cutter (90) described above. In an alternative version, the ring of magnets (900) may be located adjacent to transfer member (22) such that marker deployment tool (800) may be attracted to the ring of magnets (900) when tissue sample holder (100) is removed. In such a version, the ring of magnets (900) may be located proximally of transfer member (22) or distally within transfer member (22). In the version having the ring of magnets (900) located distally within the transfer member (22), a funnel (not shown), may be provided to possibly aid in guiding marker deployment tool (800). Further still, the ring of magnets (900) may be impregnated within a portion casing (80) near transfer member (22) or tubular cutter (90). Magnets (900) may be configured for any other suitable location on a biopsy device to facilitate the guidance of marker deployment tool (800) for use in deploying markers within a patient's body as will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, the biopsy device comprising:
   (a) a probe assembly, wherein the probe assembly comprises:
      (i) a needle, and
      (ii) a cutter, wherein the cutter is movable relative to the needle to sever a tissue sample; and
   (b) a tissue sample holder coupled with the probe assembly, wherein the tissue sample holder comprises:
      (i) an outer cover,
      (ii) a rotatable manifold, wherein the rotatable manifold defines a plurality of chambers, wherein the rotatable manifold is movable to selectively index each chamber of the plurality of chambers with the cutter of the probe assembly, and
      (iv) a plurality of tissue trays, wherein each tray of the plurality of tissue trays is insertable into a corresponding chamber of the plurality of chambers of the rotatable manifold; and
   (c) a transfer member, wherein the transfer member is disposed between the cutter of the probe assembly and the rotatable manifold, wherein the transfer member is configured to communicate tissue samples from the cutter to each chamber of the plurality of chambers of the rotatable manifold when each chamber is indexed with the cutter.

2. The biopsy device of claim 1, wherein the transfer member comprises a first aperture and a second aperture.

3. The biopsy device of claim 2, wherein the first aperture is positioned adjacent to a chamber of the plurality of chambers.

4. The biopsy device of claim 3, wherein the transfer member comprises an elongate portion extending distally from the first aperture.

5. The biopsy device of claim 4, wherein the elongate portion is configured to receive the cutter of the probe assembly, wherein the elongate portion is configured to permit translation of the cutter within the elongate portion.

6. The biopsy device of claim 2, wherein the second aperture is configured to communicate vacuum to the tissue sample holder.

7. The biopsy device of claim 6, wherein the body of the probe assembly further comprises a vacuum line, wherein the vacuum line is in communication with the second aperture of the transfer member.

8. The biopsy device of claim 1, wherein the transfer member is resilient.

9. The biopsy device of claim 1, wherein the transfer member is configured to seal at least a portion of the rotatable manifold relative to the probe assembly and the rotatable manifold is rotated.

10. A biopsy system, wherein the biopsy system comprises:
(a) a biopsy probe comprising a cutter and a needle, wherein the needle includes a lateral aperture, wherein the cutter is configured to move relative to the lateral aperture of the needle to sever a tissue sample; and
(b) a tissue sample holder coupled with the biopsy probe, the tissue sample holder comprising:
  (i) a rotatable manifold, wherein the rotatable manifold comprises a plurality of chambers, wherein each chamber of the plurality of chambers is configured to receive a tissue sample from the cutter of the probe,
  (ii) at least one tissue sample receiving tray carried by the rotatable manifold and removable from the rotatable manifold, and
  (iii) an elastomeric sealing member, wherein the elastomeric sealing member is positioned distally relative to a distal end of the rotatable manifold, wherein the elastomeric sealing member is configured to direct fluid along a vacuum path through the rotatable manifold from a first port to a second port disposed in the elastomeric sealing member, wherein the elastomeric sealing member is further configured to communicate tissue samples from the cutter to a chamber of the plurality of chambers of the rotatable manifold.

* * * * *